United States Patent
Guo

(10) Patent No.: US 10,184,125 B2
(45) Date of Patent: *Jan. 22, 2019

(54) MODULATION OF TMPRSS6 EXPRESSION

(71) Applicant: Ionis Pharmaceuticals, Inc., Carlsbad, CA (US)

(72) Inventor: Shuling Guo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/850,093

(22) Filed: Dec. 21, 2017

(65) Prior Publication Data

US 2018/0223289 A1    Aug. 9, 2018

Related U.S. Application Data

(63) Continuation of application No. 15/343,104, filed on Nov. 3, 2016, now Pat. No. 9,885,047, which is a continuation of application No. 14/356,863, filed as application No. PCT/US2012/063970 on Nov. 7, 2012, now Pat. No. 9,725,722.

(60) Provisional application No. 61/556,755, filed on Nov. 7, 2011, provisional application No. 61/710,636, filed on Oct. 5, 2012.

(51) Int. Cl.
| | |
|---|---|
| *C07H 21/02* | (2006.01) |
| *C07H 21/04* | (2006.01) |
| *A61K 31/70* | (2006.01) |
| *C12N 15/113* | (2010.01) |
| *A61K 31/713* | (2006.01) |
| *A61K 45/06* | (2006.01) |
| *C12N 5/00* | (2006.01) |

(52) U.S. Cl.
CPC ........ *C12N 15/1137* (2013.01); *A61K 31/713* (2013.01); *A61K 45/06* (2013.01); *C12Y 304/21* (2013.01); *C12N 2310/11* (2013.01); *C12N 2310/315* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

2014/0194489 A1* 7/2014 Bumcrot ............. C12Y 304/21
514/44 A

OTHER PUBLICATIONS

Singh et al., International Journal of Pharmacology vol. 7(3):294-315, May 18, 2011.*

* cited by examiner

*Primary Examiner* — Sean McGarry
(74) *Attorney, Agent, or Firm* — Knobbe, Martens, Olson & Bear, LLP

(57) ABSTRACT

Disclosed herein are antisense compounds and methods for modulating TMPRSS6 and modulating an iron accumulation disease, disorder and/or condition in an individual in need thereof. Iron accumulation diseases in an individual such as hemochromatosis or β-thalassemia can be ameliorated or prevented with the administration of antisense compounds targeted to TMPRSS6.

20 Claims, No Drawings

Specification includes a Sequence Listing.

```
                         SEQUENCE LISTING

<160> NUMBER OF SEQ ID NOS: 20

<210> SEQ ID NO 1
<211> LENGTH: 3206
<212> TYPE: DNA
<213> ORGANISM: Mus musculus

<400> SEQUENCE: 1
agtttcattg tcgccctgga cctgacagga gaggcccatg gaacttgggg ccacaggcca     60
caagggacaa gggccagaca ccccagccat ggctccaggc cattgatcca acctaagctg    120
gccagttggg ggtggaaaga ccttggcctg gataaacaga ggcctccagg cctgtgtgca    180
ggcccggcac ctaccttcca ctcttgaaga tgccgagatg tttccagctc ccctgttcta    240
ccaggatgcc caccaccgag gtcccccaag cggctgatgg tcagggcgat gcgggtgatg    300
gagaggaagc tgctgagcca gaggggaagt tcaagccccc aaaaaacacc aagagaaaaa    360
accgggacta cgtccgcttc acgccactgt tgctggtctt ggctgcgctg gtctcagcag    420
gggtcatgct ttggtatttc ctagggtaca aagcggaagt gaccgtaagc caggtgtact    480
ctggcagcct ccgggtgctc aaccgtcatt tctcccagga cctgggccga cgggagtcta    540
ttgctttccg cagtgaatct gccaaagccc agaagatgct ccaagaactg gttgccagca    600
cccgcctggg tacttactac aactctagtt ctgtctactc ctttggggag ggaccccctca   660 cctgcttctt ctggtttatc cttgacatcc ctgagtacca gcgactgacc ctgagccctg    720
aagtagtgcg cgagctcctg gtggatgagc tactgtccaa cagctcaacc ctggcttcct    780
ataagaccga atatgaggtg gacccggaag gcctggtgat cctggaagcc agtgtgaacg    840
acatagtcgt actgaattcc acgctgggct gttatcgcta cagctatgtg aacccaggcc    900
aggtcctccc attgaagggg cctgaccagc agaccacaag ctgcctgtgg catctgcaag    960
ggcccgaaga cctcatgatc aaagtgcggc tggagtggac ccgggtcgat tgcagagaca   1020
gggtggcgat gtacgacgca gctgggcccc tggagaagag acttatcacc tcggtctatg   1080
```

```
ggtgcagccg ccaggaacct gtgatggagg tgctggcatc gggctccgtc atggccgtgg      1140
tgtggaaaaa gggcatgcat agctactatg acccttcct gctctcagtg aagtctgtgg       1200
ccttccagga ctgccaggtg aacctgacac tggagggccg gctggacaca cagggcttcc      1260
tccgtacacc ctactacccc agttactact ctcccagtac ccactgctcc tggcatctca      1320
cggtaccctc tctggactac ggcttggcgc tctggttcga tgcctacgca ctgaggaggc      1380
agaagtacaa ccgactgtgt actcagggcc agtggatgat ccagaacagg aggctgtgtg      1440
gcttccgtac cctgcagcca tatgctgaga ggatccccat ggtggcctca gatggtgtca      1500
ccatcaactt cacctcccag atctccctca caggcccggg tgtgcaagtg tactacagct      1560
tgtacaacca atcagacccc tgccctggtg agttcctctg ctctgtgaat ggactgtgtg      1620
tccctgcgtg tgacgggatc aaggactgcc caatggcct ggatgagaga aactgtgtct       1680
gcagagccat gttccagtgc caagaggaca gcacgtgcat ttcactgcct agagtctgtg      1740
accggcagcc cgactgtctc aatggcagtg acgaagaaca gtgccaagaa ggagtgccct      1800
gtgggacatt cactttccag tgtgaggacc ggagctgtgt gaagaagccc aacccagagt      1860
gtgacggcca gtcagattgc agagacggct cagatgagca acactgtgac tgtggcctcc      1920
agggcctctc cagccgtatt gtgggcggga ccgtgtcctc cgagggtgag tggccatggc      1980
aggccagcct ccagattcgg ggtcgacaca tctgtggggg ggctctcatc gctgaccgct      2040
gggtcataac ggccgcccac tgcttccagg aggacagcat ggcctcccg aagctgtgga      2100 ccgtgttcct gggaaagatg cggcagaact cgcgctggcc aggcgaggtg tccttcaagg      2160
tgagccgtct gttcctgcac ccgtaccacg aggaggacag ccatgactac gacgtggccc      2220
tgctgcagct cgaccacccc gtggtgtact cggccactgt gcgcccgtc tgcctgcctg       2280 cccgctccca cttctttgag ccaggccagc actgctggat cacaggctgg ggagcccagc      2340
gagagggtgg tccggtgagc aacaccctgc agaaggtgga cgtacagctg gtccctcagg      2400
acctctgcag tgaggcctac cgctaccagg tgtccccacg catgctctgt gctggctacc      2460
gcaagggcaa gaaagatgcc tgccagggtg actctggagg cccactggtt gcagggagc       2520 ccagtggccg ctggttcctg gcagggttgg ttagctgggg cctgggctgt ggccgaccca      2580
atttctttgg cgtctacacc cgtgtcacac gtgtgatcaa ctggatccag caggtgctga      2640
cctgagggct gttctacaga gctggacctg cctccaggcc aagttcaggg tgtccaccca      2700
gccaggacac aagtattctg gggcaagtga ccctgctaag gcctgtttcc ctcaggccta      2760
ccccagtgac agtacagaga aggatgtcag ctggtggtta ggatgcctcc tgaggtccag      2820
gggccagcct cggctaggtt tcacttctaa ccctttctta ttctagtcct ttcccctccc      2880
tgctcctacc actgttttgg agtggggtct ggcggccatg accttggcct ccgggtctct      2940
gtaggaaaga aagaatcctt cccttgcaa aagcctcttg ggggaactgc acagagaaag       3000
aaggtgcctc tatcaaggct ctatcagagc ccttgagtct gccaagtggg ctgtactcta      3060
agccaaatca ccgggcagcc tcagctgcag atgcctgctg aagctctgcc tgctacaggg      3120
gcctccctgc cattcactgg aggcccactg tctgttctgg aataaagca cttgaccaag       3180 ccctgacact gaaaaaaaaa aaaaaa                                            3206

<210> SEQ ID NO 2
<211> LENGTH: 3212
<212> TYPE: DNA
<213> ORGANISM: Homo sapiens

<400> SEQUENCE: 2
```

```
cttgagccag acccagtcca gctctggtgc ctgccctctg gtgcgagctg acctgagatg    60
cacttccctc ctctgtgagc tgtctcggca cccacttgca gtcactgccg cctgatgttg   120
ttactcttcc actccaaaag gatgcccgtg gccgaggccc cccaggtggc tggcgggcag   180
ggggacggag gtgatggcga ggaagcggag ccggagggga tgttcaaggc ctgtgaggac   240
tccaagagaa aagcccgggg ctacctccgc ctggtgcccc tgtttgtgct gctggccctg   300
ctcgtgctgg cttcggcggg ggtgctactc tggtatttcc tagggtacaa ggcggaggtg   360
atggtcagcc aggtgtactc aggcagtctg cgtgtactca atcgccactt ctcccaggat   420
cttacccgcc gggaatctag tgccttccgc agtgaaaccg ccaaagccca gaagatgctc   480
aaggagctca tcaccagcac ccgcctggga acttactaca actccagctc cgtctattcc   540 tttgggagg accccctcac ctgcttcttc tggttcattc tccaaatccc cgagcaccgc   600
cggctgatgc tgagccccga ggtggtgcag gcactgctgg tggaggagct gctgtccaca   660
gtcaacagct cggctgccgt cccctacagg gccgagtacg aagtggaccc cgagggccta   720
gtgatcctgg aagccagtgt gaaagacata gctgcattga attccacgct gggttgttac   780
cgctacagct acgtgggcca gggccaggtc ctccggctga aggggcctga ccacctggcc   840
tccagctgcc tgtggcacct gcagggcccc aaggacctca tgctcaaact ccggctggag   900
tggacgctgg cagagtgccg ggaccgactg gccatgtatg acgtggccgg gcccctggag   960
aagaggctca tcacctcggt gtacggctgc agccgccagg agcccgtggt ggaggttctg  1020
gcgtcggggg ccatcatggc ggtcgtctgg aagaagggcc tgcacagcta ctacgacccc  1080
ttcgtgctct ccgtgcagcc ggtggtcttc caggcctgtg aagtgaacct gacgctggac  1140
aacaggctcg actcccaggg cgtcctcagc accccgtact tccccagcta ctactcgccc  1200
caaacccact gctcctggca cctcacggtg ccctctctgg actacggctt ggccctctgg  1260
tttgatgcct atgcactgag gaggcagaag tatgatttgc cgtgcaccca gggccagtgg  1320
acgatccaga acaggaggct gtgtggcttg cgcatcctgc agccctacgc cgagaggatc  1380
cccgtggtgg ccacggccgg gatcaccatc aacttcacct cccagatctc cctcaccggg  1440
cccggtgtgc gggtgcacta tggcttgtac aaccagtcgg accctgccc tggagagttc  1500 ctctgttctg tgaatggact ctgtgtccct gcctgtgatg gggtcaagga ctgccccaac  1560
ggcctggatg agagaaactg cgtttgcaga gccacattcc agtgcaaaga ggacagcaca  1620
tgcatctcac tgcccaaggt ctgtgatggg cagcctgatt gtctcaacgg cagcgacgaa  1680
gagcagtgcc aggaagggt gccatgtggg acattcacct ccagtgtga ggaccggagc  1740 tgcgtgaaga agcccaaccc gcagtgtgat gggcggcccg actgcaggga cggctcggat  1800
gaggagcact gtgactgtgg cctccagggc ccctccagcc gcattgttgg tggagctgtg  1860
tcctccgagg gtgagtggcc atggcaggcc agcctccagg ttcggggtcg acacatctgt  1920
gggggggccc tcatcgctga ccgctgggtg ataacagctg cccactgctt ccaggaggac  1980
agcatggcct ccacggtgct gtggaccgtg ttcctgggca aggtgtggca gaactcgcgc  2040
tggcctggag aggtgtcctt caaggtgagc cgcctgctcc tgcacccgta ccacgaagag  2100
gacagccatg actacgacgt ggcgctgctg cagctcgacc accggttggt gcgctcggcc  2160
gccgtgcgcc ccgtctgcct gccgcgcgcg tcccacttct cgagcccgg cctgcactgc  2220 tggattacgg gctggggcgc cttgcgcgag ggcggcccca tcagcaacgc tctgcagaaa  2280
gtggatgtgc agttgatccc acaggacctg tgcagcgagg tctatcgcta ccaggtgacg  2340
```

```
ccacgcatgc tgtgtgccgg ctaccgcaag gcaagaagg atgcctgtca gggtgactca    2400
ggtggtccgc tggtgtgcaa ggcactcagt ggccgctggt tcctggcggg gctggtcagc    2460
tggggcctgg gctgtggccg gcctaactac ttcggcgtct acaccgcat cacaggtgtg    2520
atcagctgga tccagcaagt ggtgacctga ggaactgccc ccctgcaaag cagggcccac    2580
ctcctggact cagagagccc agggcaactg ccaagcaggg ggacaagtat tctggcgggg    2640
ggtgggggag agagcaggcc ctgtggtggc aggaggtggc atcttgtctc gtccctgatg    2700
tctgctccag tgatggcagg aggatggaga agtgccagca gctggggtc aagacgtccc    2760
ctgaggaccc aggcccacac ccagcccttc tgcctcccaa ttctctctcc tccgtccct    2820
tcctccactg ctgcctaatg caaggcagtg gctcagcagc aagaatgctg gttctacatc    2880
ccgaggagtg tctgaggtgc gccccactct gtacagaggc tgtttgggca gccttgcctc    2940
cagagagcag attccagctt cggaagcccc tggtctaact tgggatctgg gaatggaagg    3000
tgctcccatc ggaggggacc ctcagagccc tggagactgc caggtgggcc tgctgccact    3060
gtaagccaaa aggtggggaa gtcctgactc cagggtcctt gccccacccc tgcctgccac    3120
ctgggccctc acagcccaga ccctcactgg gaggtgagct cagctgccct ttggaataaa    3180
gctgcctgat caaaaaaaaa aaaaaaaaaa aa                                  3212

<210> SEQ ID NO 3
<211> LENGTH: 41251
<212> TYPE: DNA
<213> ORGANISM: Homo sapiens

<400> SEQUENCE: 3
atagtaagag gagatgaact tcgcagtagt ctggagcctt tgctctcccg gtgggtgggt     60
caaaggcttt ctctgtactg tggggaaacc tgcgtcaaag gccaaataca ttgggatgtt    120
tgcttgaaag ggtctcaaaa tagagttgga accctggagc gtggagaggg gcgacattca    180
gttgctattt aatcatgatt tgttaattaa cagctcattt atgggaggca tcttagattc    240
gtggaaaaag cagggagtca gacatctaga ctcaacctcc acttccctgc tgtgtgatct    300
tgggcaagcg gcttagcctc tctgggcttc agggtttttt taatctgtaa aatgcgtctg    360
ggagtgaatg tcaggtattc aaatcacact gggaaaatgg ggctaggaaa agccctagac    420
tgagttagtg ctagaacact ctgggtctca gtttccttat ctgttcaatg ggtgcagaac    480
tggaggttta agtgagataa agcaggtgaa gtacccacgt ggtgtgggct ggaggaagaa    540
aacatgggac aatggttcca catccctggg tgacctgaaa attaagtgtg agatgtctca    600
tgagggcacg aaatgaatat tagttttgt tcccttcctc tgccacaaga ctttgagagc    660
agaaaggtga gagagacggt actctgtgaa ggaaggcagg tccccggccc agcgcagtgc    720
cagctcaggg gattctgggg cggggctaa gtgcatggac tgtgtgggcg tggtgggaag    780
ctccgtgaac cagaaccagg agcaagaaac agcattcctt gcgtggacgg gaaatgaggg    840
caagaggtca gatgtctaca gaagtctgca ccccatgtac ttcagttctg tctgtgggtg    900
cagcctctag ggaggtgggt gtttaggtac tgagacctcc gtctgtcctc tgaccatagg    960
gaagccagtg ggaagcaaag gtggggttct tgagccagac ccagtccagc tctggtgcct   1020
gccctctggt gcgagctgac ctgagatgca cttccctcct ctgtgagctg tctcggcacc   1080
cacttgcagt cactgccgcc tgatgttgtt actcttccac tccaaaaggc agggaagtcc   1140
tgcttccgtg ccccaccggt gctcagcaga ggctcccttg caaatgcgag gctgtttcca   1200
actttggtct gtttccctgg caggatgccc gtggccgagg ccccccaggt ggctggcggg   1260
```

-continued

```
caggggacg gaggtgatgg cgaggaagcg gagccggagg ggatgttcaa ggcctgtgag    1320
gactccaaga gaaaagcccg gggctacctc cgcctggtgc ccctgtttgt gctgctggcc    1380
ctgctcgtgc tggcttcggc gggggtgcta ctctggtatt tcctaggtaa cgttgtggga    1440
ccgcctggga gaggcacctg ggaggactt ggggtgactg tagcaggcac agcaggacag    1500
gactgggttc caggctcagc cgtgcttagc atattgctgt gtgaccttgg caagtcact    1560 tctgttctct gggtctccct ccctgtcctt ccagctggag atgctgtcag accctggctc    1620
caggtcctat ggctcgggtc tgcttcctgc ttgggcaaag tgccccaaag ctccccacca    1680
ggtggggaaa gtgggccctc ctagcaccca gttcttgtga ccagccagc ccacagagca    1740 taaacatcgc cttcccttgc ctgcagtcct cctgggttgc ccctgaggct tggagccaac    1800
ccagccctaa agaaggaggc ccagaggcac caatggtacc tggtaccaat tagtgcctct    1860
gctcacttga gcctagccta ggttctcctc taggctgggg accacagctc tatcccctct    1920
gggtctccag ggtccagcat gaatggggga cggagcaggc agctggagag cagccagcct    1980
tggggccctc tgccatgtcc ttaattatgg ctggcccctc cctgatgtca cagccctcag    2040
tcagtcccct ggtgcccggg gagcaattgg cctgtgctct gggcccattc atccaggcct    2100
ccgttcattc attcatggaa taaatgctct tgagcatcta ttatctttct ctaagattga    2160
tggagtctct cctcttcctt ctgcctttga cagtgggaag taatggagaa accaaatcgg    2220
actgtgcctc tacactgtac actgtagaag gcccattcat ttgttcattt actcagtgcc    2280
aagcacctcc tgtgtgccag gttctgggga tagcccctgt ccttgtgatt tagccaaggc    2340
atcagacctg acatttacgc taaagcatag catgtgatgg gacagaggaa gctgagggct    2400
gggaagccac aggagggaca acccagatgc ctgcgtgatc agaagcatcc cattaaacat    2460
cctgcaaagg atagctagtg ctcttactgg ctgaatctcc tggtggaatt ccaggcctgt    2520
tgaaagcaac ctggggacca actttgtagc agtggagaga atccatgta ggcctagatc    2580 caagggtca gggttgggag tgtctggaac cagcatctgg gagtgacact attgggaacc    2640
ccaggtctga cacgggcctg cttgcaatga cttatagtga ttctacccag agttgagcaa    2700
cgcaggcagt agacgccatg tgcatttcac caccagcagg aagccagtgc cccagatagc    2760
acagggctgt gggggcctcc tcaggtagcg ggctaattag tctacagggt aaaccacggg    2820
gcactgggct ggagggccag gaactcacct gccaattatt tctctttgca gaggagttta    2880 attcccctg attatgctcc tggggtaaat cacccccac cccaggagag gtgctccatg    2940
gggctgagga cccaaggggt gagtgctccc aagcctctgc tggggaagc caactccccc    3000 acagagggat taagggttga aggaggcact ttgggagctg tttgaaagac tcctcccgcc    3060
ttgaccaggc tgtgctcctg ggactgggcg ctgggcaagg aagtggatca gagacacgcc    3120
ctgccctgtc tggaagagga ggtgcacaag tgaccagtga cactggagca ggacaggccc    3180
caagcgagga ggacagcctg gcccgaggag agggtgtggc tggcttccta aggatggtag    3240 caggacccctt aataccacca accatatttc ctgggtcctt tcccttttcct gctctcccag    3300 gcaagagttt tatgtgttct caagccccca gcacccgcct gccctgtct cctgcttcag    3360 tgagaaaaca aaacagctta agagagaagc cccatatatg ttggcccacc tgccctccca    3420
gctgcatcac gtgcactcct cctgggaccc cgatcccgcc ccctctgccc acacaatggc    3480
ccagcaccag caaggatgcc ctctctcccc cagtgtccct tggggtgcct cccccatttc    3540
tctgctcctt gaaagagctg tcagtccaca cacccagtct ctctgtgccc tttccaacct    3600
```

```
ggctccctct gcccccaac tccaatggcc attgtcaagc tcgccaacat cccaggttgc    3660
taaatccaat gtccacttct cagtcatcat tgcacttgac ccgggggctc accccaccct    3720
ccagaagccc tttcctccct agactttggg ccgccaccgg gtcctttccg ctcagcaggt    3780
tgcttttcct gtgtccctgc tgatgggtgg ggcctctcct ttctctctcc accgcttct    3840 ttcgtgatct catctgctac ccttagcttc aagtgcctt tataccctga taacacccac    3900
atttgcattt ctagcctggg cctctcctt gagcttgtct ctagagctgc ccctgctctt    3960
cctcttaatg tctaaggagc atctcggacc ctatgctttc agaccatgag gtctctgcat    4020
aatttccccc agacctgtac ctccaacatc ccagtccaag accacttctt tctggcacct    4080
tccccttact cctttctttc ttttccaccc agccccactt tgccagcaaa cctggtcatc    4140
tctaactcca aaacacatca aaagcagctg acgccaatca cttccacccc tctcctctgc    4200
cacagctggg gccaggctct gtcccctgg acatctctcc cctggagccc tgcaggcgtg    4260
tcctcgatgc tctccctgcc tctgccctgc ctccttagag ccttctcaa cagcagaggg    4320 accatttgat aaagcaaacg aaatcctcta acttcgctgc ttaaaacctc gcttggggcc    4380
aggcgcgtgg ctcacgcccg taatcccagc actttgggag gccgaggcag atggatcacc    4440
tgaggtcagg agttcgagac cagcctgacc aatatgcaga aaccctgtct ctactaaaaa    4500
tacaaaatta accgggcgtg gtggtgcatg cctgtaatcc cagctacttg cgaggctgag    4560
gcaggagaat cgcttgaacc cgggaggcag aggttgtggt gagcggagat tgagccattg    4620
cactccaagc taggcaacaa gagcgaaact ctgtctcaaa acaaaacaa aacaaaaaca    4680 aaaagaaaac aaaaaaacca cctcccattc ctcccatctt acccagggtg aaagcccgag    4740
tcctcccagg cctggaaagc cctacccagc ctctccctt cccatctca taccctcctg    4800 ctgtcctgtt gctcactctt tgctgctcct gaaacacacc aggcctttgc acttgccct    4860 gcctgggaca ttctttccac agatgtacat caccttcttc cctgacctcc atatcgcagc    4920
ccgtcccatg ccctgattcc caccgcactg accacctcta acctgttata cacgatgtgt    4980
ggtttaccgt ctgattcctt gctagtctac aagctattaa gggcagtttt tcttgatag    5040 ttctgtccgt tgttttgctc atatagtccc aagtactttg gctcagttcc tacacatagc    5100
aggctctcaa gaggtatta ctgagtaaat ggataggggt gtaaaccagg gctgtgagtc    5160
taccctcttc acttcagcca aaatagcctt tgcaaaacag aagtctgatg acatcattcc    5220 tgatttaaa cttttcatgg ttaccttgt tcatcgggta aagacccaat gggccctgcc    5280
ctgcggaggc cccagctcct tgccgcccct cccatctct gactgctcca gccaaacagg    5340 cttcagccc gggtcctcac catggtcccc gtgctaccgg ccccgtgccc catgctgctc    5400
cctctgctgg aagtactc cctccctctt ctcttaccaa tttacagttt ccccatccct    5460
acatctcagc tggagggtca ctccactctg gcccaggctg agtgtcctcg tcacatcccc    5520
tcaacagcac catgtggcac tgctccctga tggcactgcc cacagacaga tgccacatgc    5580
tgtgtggttg ccagagccac gccttttctta cccaccactg tcagcttcac aaggggaggc    5640
acatctgtct tggttaactg gcgtaccca tgtagtaggt ggttagcaca cactgtggga    5700
tccctgggtg acctcacgag tggaaggatg cctagtggtg ctgacccatg accttggcct    5760
cctgggccta tgtggatttc ctggccttca tgtcattggt gtcctggact ggtcactgtg    5820
tcagcctctc cctgggaacc tgtaggacac catccatctg ggagcctttc acctccctgg    5880
taccttgcag ccagtttgtc atccaataaa ctttagatga ccatgatgac aatgggagtg    5940
acaaagatga tgatgatgac attgatggtg ccatggagac ccaagacact gaggctgagc    6000
```

-continued

```
tgagggtgtg ggtggcagga gaaggcatgg aagagacagg agactttccc acctgcttcc    6060
tccactaacc ctgctggttc cttcctgggc agggtacaag gcggaggtga tggtcagcca    6120
ggtgtactca ggcagtctgc gtgtactcaa tcgccacttc tcccaggatc ttacccgccg    6180
ggaatctagt gccttccgca gtgaaaccgc caaagcccag aagatggtag gaaaggatct    6240
gggggatgag agggagggaa tatggggggtg aaaagagagg ggtggggtct gatcacatgg   6300
agccagttgg tcaacccatc tggagcattc acagggacca cagccctgct ccaggcacca    6360
tggaagcaga tgaggttgag ggtcatggga aagttagtgg atgtttgggt caatagcact    6420
cggattagat cctgatcatg cctcttacca ggggtggagc atgaccttgg gaaaggtccc    6480
acagtgcagc tgacactatt gagggcccgc tcctgcccct ccgttacagg acggtggccc    6540
gctcctcccc ctccgttaca ggacggtggc ccgctcctcc ccctccgtta caggacggtg    6600
gccgctcctg cccctccgtt acaggacggt ggccgctcct gcccctccgt tacaggacgg    6660
tggcccgctc ctcccctcc gttacaggac ggtggccctc tcctcccct ccgttacagg     6720 acggtggccc tctcctcccc ctccgtaaca ggacggtggc cctctcctcc ccctccgtta    6780
caggacggtg gccgctctt cccctccgt tacaggacgg tggccgctcc tgcccctccg      6840
ttacaggacg gtgcccact cctgcccctc cgttacagga cagtggccgc tcctgcccct     6900
ccgttacagg acggtggccc gctcctgccc ctctgttaca agacggtggc ccgctcctgc    6960
ccctccgtta caggacggtg gccactcctg cccctctgtt acaggatggt ggctcactgc    7020
acggaggctg gtctactgcc tgccactctc aggctgcagg accactgccc agcaaggcag    7080
gccagaagtg ccggggagtt attcccagga gcaaccctga accatgagcg ctggagtggg    7140
tggatcaata ccgcagcttc tttgccctg caggggggaa tagttcacag aatgttccag     7200
gctgtctccc agagatgccc tattcggctg agctcagatg ctctcagctc tacactgcgc    7260
attcatggcc ctgtgttggt tgcccacttt ccagtctctc cctcccaact actgtttccc    7320
agaatcacct ccaaataaac cacttgcccc accttgtcaa tggagggtct gcttctgagg    7380
gacccagcct gaggctgccc gtttcctcct ccatgaggta ggggtgataa caacaggacc    7440
cggctgcaga tttgttgtgg gttgcagtga agttgagata acacgaacac tattcccacg    7500
ctgcgcaaat gcttaagagc ctgtaatcct gccagcagcg ctgtagttgg agatgcgcaa    7560
aaactaccca tcagagctgc tggcttgtcc caggccatgg gaggaggtgc agaggggacc    7620
caggagccga gtggggtttc tcagagttga ggagtgactt ttggcaaggg gcagaggggt    7680
catcagcagt gcaggtggag gtgagagtcg ggtgtagtgg aaacagaaag aaggggatgg    7740
ggtgtgagat tcatgcatgc cccggcccgg ccactcagca ctgtgtgacc gtgatcaagc    7800
ctgtccacct tggagaatca tgcatggagc ggggctgcca gtaggagcaa agggcacctc    7860
caggtaggaa gtgggcctgt ctgccctgca gagggtccca ggggctgttg tcttcccttc    7920
tcacagctca aggagctcat caccagcacc cgcctgggaa cttactacaa ctccagctcc    7980
gtctattcct ttgggtgagt tgtccttgcc cctgaccagc tcctgcaaga agctgagatt    8040
caaagaatgg gaggggcctc tgtaggcttc tgatgcaatg ccttcatgtt tcaaatgggg    8100
aaactaaggc atagagaggg aacttggctt cctgcatgtc accctccctt cactgggctc    8160
atctgtagaa tggaaacatg ggtgtgatag gtttgcacca gacaatgact gtgatggctg    8220
atcaagggcc tgcaccatc aggcgaggcg atgttggagg ggcatggggt taaaagcatt    8280
ggctccaggg cccgactgcc ccgtccacat ctggttctgc tacttgcggc atagtttatg    8340
```

```
agacacaagt tcacctctca tgcctcagtt ttctcattcg taaaataagg attatgagag      8400
cgcctccttc agaggtcgct aggaggcttc tgcgtgaaga cggacagcaa tggctgaggt      8460
gcggaaagtg ctcgatgtgc atgagcaggg gtggagctgg ggccagacct cagaatcctt      8520
ccctggcctc tctcacttct gcctgcctta gggagggacc cctcacctgc ttcttctggt      8580
tcattctcca atccccgag caccgccggc tgatgctgag ccccgaggtg gtgcaggcac       8640
tgctggtgga ggagctgctg tccacagtca acagctcggc tgccgtcccc tacagggccg      8700
agtacgaagt ggaccccgag ggcctagtga tcctgggtca gtactgcgag tggaaacgtg      8760
gggttggcct catgaggttg ggggaaacaa gctgtggtgt ggcccgggga ggctgcctgc      8820
caggcctggg gtgctgtcag ggtgggcccc ccaggagagc cccccaggtg aggtagcagt      8880
gccattgcat tcaaggagcc aggaaagaag ggtgggatgg gggcatttag ggtaaatctc      8940
agacaaggct ggctccaagg gtctcctcta atttttatttt cattgtattt tctttttcttt    9000 tttttttttt ttgttcttgt ttatttgttt gttcatttcc ttttatcaga agccagtgtg      9060
aaagacatag ctgcattgaa ttccacgctg ggtacgctat ttttttttcc cctccccatt      9120
ttccttttga gttggcattt gtcttgactt tgttgtgtat caggggggaca catggcttct     9180 gttgtgtgtg cagggagccc tggccaagag tcacccaggg gatgccatgg tggactcagc     9240
gatgtgtccc aagcaagtct tggagcctgt aggggagag gaggtggcga cgtgcatgcg      9300
tgtatttgtg tgtgtcttgt agacgggtgt gcatgcgttc ctgtgtgggt gtgaggatga     9360
gtcaggttta gtggtccacg aacgtgactc tcctctatca ttcacttcaa cctgcccaca     9420
agctagtttc cactgatggt agaaaatcat cttgccaatt cacggtttgt cagtcacgtt     9480
ggttttaaaa cttggtcttt tggaggtagc ggtgccattg cattcaagaa cgctccttcc     9540
ctcttttcct ttccttccca gtcaggctca tcagccctcc ctcccttacct ggtgccgtat    9600 tgctagagtc accttgcatt tctccaagcg acccacaat cttttcagctg accagcacag     9660 tcaccacgct gcacaaggca ggaggtgctg tccaagttgt agtttgtgtg agttgtgcag     9720
tgcaccaact ggctgctgga ctctatggcc cctaaattct cagattcctc ccacactatc    9780
tagtgttgtc acccagagcc aaggtgggg tgagcgtctc aaccccttct cagggaggga     9840
ggcagagttt aaatccttgt tatacctttc cttaccttcc cgtcttccca tcctgctggt    9900
caaatgcttg cttctttgtt ggatggaggt gatgaggtca aagtacagtt ttcaaagagg    9960
tgaaatcatg attctcatac aaagatagag tgaccatgtg tcaaatattt atttggctga    10020
ttaatggggg aacgagtaga atggtaaaga atgcaagaaa ctgatctatt tgtctatcta   10080
tctatctatc tatctatcat ctctgttgat atctgtctgc ttgtctatct agttatctaa   10140
ctagctagct gtctattatc tatctgtctg tctctctgtc tctgtctgtc tagctagcta    10200
gctgtctgtt tatatctatc tatctatcta tctatctatc tatctatcta tctatctatc   10260
atcaatcatt aatggaaaaa gagaattgct agaataagat taccaagtta gatcaaaacc   10320
tggttaaggt cctaccaggc aagaaaactc aaacctttgg agttgtcttt tctagtgaat   10380
taaaatcatt gacagcttat tacagtcttc tgaaagttaa catctacctc tacagagtct   10440
gaggttgata atctacaacc aatagtaagt cagagatatt actcctgaga gcctcagggg   10500
gacttaatca gatgatgctt ggagacagag actggctcat tgcagcctgg acaccgaatc   10560
tggtcaattg ctgcctgatt ttgtatagcc catgagccaa gaatgacata tatatatata   10620
taacagagtc tcactctgtc atccaggctg gagtgcagtg ccgcgatctt ggctcattgc   10680
aacctccacc tcccaggttc aagcaattct cctgcttcag cctcctgagt agctgggact   10740
```

```
acaggtgcct gccaccatgc ctggctaatt tgtatatttt tagaagagat gaggttttgc   10800
cgtgttggcc aggctggtct cgagctcctg acctcaggtg atccacctgc ctccacctcc   10860
caaagtgctg ggattacagg tgtgagccac cacgcctggc tccataggcc atttttcaat   10920
tattaaaaaa tataaaagtc agccaggcat ggtggctcat gcctgtaacc cagcactttg   10980
ggaggcagag gcaggcagat cacctgaggt caggagtttg agaccagcct ggccaagaag   11040
gcgaaacccc gtctcttcta aaatataaaa aattagccgg gcatggtggt gcgcacctgt   11100
agtcctaacc agtcaggagg ctgaggcagg agaatcactt gaacccggaa gatggagctt   11160
gcagtgagct gagattgtga ggttgtgcca ctgtactcca gcctgggcga cagagtgaga   11220
ctccatctca aaaaaaaaa aaaaaaaaa aaaaaagaa agaaagaaag gaaggaaaa      11280
ggtcctatgg aaagttatttt tttctcctgc aatagaagtg ctatgtaata gcctcatgtt   11340
gcctcgtgcc tctgtgtccc catgttcctg gcagttgttc tgtaattatc tgtgctcagt   11400
gggtgttcgt ttcatgaatg aatgattgaa caaatgaatg aaagcatgaa tgaggagact   11460
ggttcagtgc atgtccagag cacagagtct caggggcag agataacaac tcaaatcctt   11520
gaagtcgact ttatgagcac ttccttcatg ccaggcccca ttcctgcgct gaggacacca   11580
ggatgaccgt gtcctcaccc ctgccctcgg aggagcttta agccccatga gggagacaga   11640
cacataaaca gattctcata acaccaggtg ccagtgtgag aatagaggcc ccagaggcag   11700
tggagagagg gaattgttcg ttccaaagca gaagaggggg caaatcaaga gcctcacaca   11760
gagtcccaga tctacaggag ggaggggttg ctcctgactg ggggatcctg gaagacttca   11820
tggagggggc atcagatttg ggcatgggcc gggcgtggtg gcacaagcct gtaatcccag   11880
cactttggga ggccaagttg agcggatcac ctgaggtcag gagttcgagg ccagcctggc   11940
caacatggca aaacccccatc tctactgaaa atacaaaatt agctggtcat ggtggcccat   12000
gcctgtaatc ccagctactt gggaggctga ggcaggagaa ttgcttgaac ccaggaggtg   12060
gaggttgcag tgagccaaga ttgcaccatt gcactccagc ctgggcagca agagcaaatt   12120
ccattaaaaa aaaaattagc tggacatggt ggtgtgcacc tgtagtccta gctactcggg   12180
ggtggggtg gggggctaag gtgggaggat cacccgagct caggaggtcg aggctgcaat   12240
gagctgttgt gatcgcatca ctgcgctcca gcctgagtga caggctgtct caacaataaa   12300
ataaaataat tttcaaaaga aaagaaatt caggcatggg ggtaggcagg aatttgtcag   12360
ggcgagaaga agaaagggtt ccctgagcag agggaatggc aggggcaaag gctgggggag   12420
gggaacaccc aaggcgtgtt cagttaattc ctcccagccc cgagaggtgc caggctcct   12480
gaaggtgttt ctgattaaca agaggttagc acacacctct ccacggaatt cgtctcaaaa   12540
aaaaaaaaa gggtaattat taaagtggca agagcaaaga atctgcttgg agcaagattt   12600
aaagaacaca aaccctagg aagagccagc catctttccc cagctgctgg tggaggccct   12660
gtcccttccc taggcagaca ttgttgttct ctctctgggg aggtcagctc cccactgcag   12720
tcagcatggc caggggtcag ggagaagggg ctgagccaca ggtggcagca tcagagcaaa   12780
gtgtattcac ctccattccc ttcctggtcc tcagcactgc ccagaggagg tcataggaca   12840
gggattatta ttcatccat ttgacagaac ttggaatggc taagccactg cccagactc   12900
agttaactac ccagaggtag tgaacatcta cctctacaga gtctgaggtt gataatctgc   12960
aaccaatagt aagtcagagt tattactcct gagagcctca gggggactta atcagacaat   13020
gattggggac agagactggc tcactgcagc ctggacaccg aatctggtcc actgctgcct   13080
```

```
gattttgtat ggcccatgag ccaagaatga catcatcaca cagctgatga gtgttggtgc   13140
taggtgggga gggtagtgcc cctccctcct tctctccagt tccctcccca tatacccct    13200 cccctggggg cccagcagat ggcactagcc tgggggggcct gccctcaggc tgaccaagct  13260 gacagggggga cttttgcttg cctgtggcct tccaaagaag acgatttaaa gcagagaaaa  13320
cagactgaaa actcaggttt tataatttca tgtcaccagg ctgcctccca catcccaggt   13380
tcattcctaa atccccactg gctcctggaa gaacaccagg cttctggcga ggtttaaatg   13440
agatactgga tgctccacgg gagagaacat gttcactggc agaccctggt gcctagatcg   13500
aacacacagt cggtgcacag tcactgtttt gaatgaatga atgaatgaat gaatgatgca   13560
ggtggtactg ctttgtaagt tctagcagtg catcagagct tacggattag atggaagagc   13620
agagactcac tggtgtgtgg ggtaggggg tgggtatga tggtgaaaca gttgtgaagt     13680
gaggcagccg tgagatgggc taggtctgag cctcaggcgg ggccagctgc aggatgaaaa   13740
gtcacaggcc tttctcccca gccctacctg ctccgtctcc ctcacaccca cctgaggaac   13800
caggcactgc ctttattgag cccctactgt gcaaggtgct gtgctgggca ttcaaacgtg   13860
tatcatccta cagcctctgc tggcggccct gcaagggtgg tgttatcgtc ccattctata   13920
gatgaggaaa gcaaggccca ggaaagatta ggtggtggct gggcaaaccc agatgtgtct   13980
ggcccaggtc tgtgcaatgg acacaatcat tgaaagtatc tcatacagct gttgtgggca   14040
ttgagcgaga cagtgaggga aggcattcag ttcagttct ggcctgtagc aaatgcttga    14100
taagcacctg ttttattctg atggcttcac catcattagc tcaaagctca tgtcctcccc   14160
ccagggcagc ctcccagact cctccttagg gcactccctt ctctctaccg gaagtgaagc   14220
cctcatccct tcttctcctc attgcctgtg gcctcgctgg tctccacagc agccagagga   14280
gtgtgtggtc caagccagcc catgtccagc cttgcccaac cttctgtggc tccctatggc   14340
tgcaggagaa agcagcgccc atcctcggaa tggcctgggc caggcctccc tgccttcagc   14400
ttgtcctcta gatacacgtg ccctgtgtgt acttttctca aagctgcccg gctcgcccca   14460
gcctctttgc tcacgcaggg accccagga tgcccccagc ccacaggccg ggtttgaagc    14520
cgtcacctcc tgagctattc ttgcctgttc tgtgtctgtc tgtccccgct gtcatccatg   14580
tccccaggca gcgactggat ttttacctgg gcactgagaa ggcgtgaagc tcagtgtgtg   14640
tccattccat gagtgaatga ctgaaccaat gaacaaatgc atgaatgagg atactgcacag  14700 ggaaagagaa ggatgggta gagcatgtct ggctatcccc acccggctcc cctgcccagc    14760
ccatcctgcc tggtggagga ccttgaggga cctggctccc cagggtcccc tccttctggc   14820
tcacaggaat caggggctgt gcccctctcc ccgctccagg ttgttaccgc tacagctacg   14880
tgggccaggg ccaggtcctc cggctgaagg ggcctgacca cctggcctcc agctgcctgt   14940
ggcacctgca gggccccaag gacctcatgc tcaaactccg gctggagtgg acgctggcag   15000
agtgccggga ccgactggcc atgtatgacg tggccgggcc cctggagaag aggctcatca   15060
cctcgtgagt ccctgggaag gagggcagga gggagggctg gaaaagggag tggttgatgg   15120
gggagttgaa agtcacacac agcattctta gacaagggag ggtaggacct tgggcctggg   15180
tatctgggag acaggacggc tagcttagag gggataggg agaggaggct ggagatggtt    15240
gtgtactggg ggcgcttccc ctccgcgagc ctcagtttcc ccatctgtaa caaagccgtt   15300
gttgtagatg actcctgaag tcagctctgg gaggcaccgt ggcttgttgg gatgtttcag   15360
agtctggctg cagcctggac tttcaacctc tgggctcgtt cctaaatcct gactgcttcc   15420
tggtagaaca cccacccctct ctgcttccca ggcttctggt ggggtttaaa tgagatacta   15480
```

```
gattccccat gggaggggat gtcttcactg ccgggccctc gtgcctagac caaacgcaca    15540
gtaggtgtgc agtatctatt ttgagtgaac gaatgaatga tgtaggtggt actgctttgc    15600
aagttctagc aatgcatcag agctcacgga ttaaatgtaa gagcagagag cttactggt     15660 gtgtggggcg ggggtgtggg gatgtgacgg ggaacccct gtctcctagc tgcgtgccct    15720
aaggcaagtt actttgcctc ttagaacctg cttaccttgc cggatcattg gaggatttaa    15780
atcagactat ctgtgccatg atccttacac atagtgagtg cctagcactt acacgctagc    15840
cattattgtt atcattatat atgctctaac tgggactggg ccgcaaaagg cattgagtgc    15900
caggagccat ttggactttg atatttggta agtggggagc tattgaaagt tcttgagcac    15960
agaagtaggg ctttagggca taagatatgg agtggagtac agaagtgatc aggatcagag    16020
ggcaggtggt tggggtggg gaggagggac tggaaatggc cttgacctct gggagcctgg    16080
tcctcccaca ggatggggag atgggtgtta gcctacaaag cactgcagga ggtggggaag    16140
atgctctggg ctgggcagtt ctcagcgatt gtttattgag cacttacttt gtgctgggcg    16200
tcaggctgat gcctcttctg tctcacttgg gctgtggcca gcctccaggc agatggggat    16260
gggaccagtg tgttcagatc aagcgcagtc tttgaatgtg agctggcaga ggttcttgcc    16320
acacccctcc cccagggcct ctccaagctg ctctctcctt gtcaccccctc ctgctgtcct    16380 gctgggtgtg acctcgatct gcggcatgtg cgtgggctga gtttctggag ggctctggga    16440
agtgcagaga agccagacac catctgactt ccaggtccaa aaagggtggg gacacttagg    16500
ggtttcccct ggggcttctc caggtgcctc tcagcctggg aggggacctg actgccaggc    16560
ccagctctgt tcctactcac tgtggctcct ggtggctctc tcatcccaga cccttggaga    16620
agctctaaaa tgacaggtca gacaacattt ggggttctca agcttgtacc ccagacacct    16680
gctagggaat gggggtgagg gggactttgg tggtgatggg aagacagagc aggtggcccc    16740
ttgctcagtt tcaaccatgt gctttgattc tgcgttccat atttcattta taagaagggc    16800
tctgccgcta ggtaaataaa ataaaacccc ccaacaatga aagctaaagc ccccattaaa    16860
ggtgacctcc aggtctcttc catcctaata tcgtatctcc cacctcccag ggaagatgag    16920
ccggtaaggc caaaaaggac gtggctgtat gggagggtgg ggggcaccgg tgtggttggg    16980
gagacttggg tgctgcagca ggaagatcaa gctggaatgg taggaagaag ggacgagggc    17040 ctgggggtg aggggggtgg tgcctgctac tggaggccac ctccctcccc tggcaagagg    17100
ccaggggaaa tgccccatcc ccggaccctg ggcaccaaga ccctcccagg gagacccttg    17160
gggttatgcc caccatgcct ccagctggct gcaggctgct tgggtgccat gtgtagcgat    17220
tttgaggctg tgcttggagg agctcaggta ctcgcttgcc aaggtgcctg aaatccctcc    17280
agcagcaccc cttcctcctg tcaaggccca ggtgcccacg cacagtctgc aggcagggag    17340
gctattgggt tgcccattca gagggaggtg gggccgttag tttcttataa attgacccat    17400
cagatgcgcg ggactccaga gagtgttgcc attgacactg ggaagtttgg gggaggttgg    17460
tgagagggtg aaggggagct ggggaacccc tgtctgagac aggcagacca ggggcaccta    17520
catatgtggg agggtaccag ccatcacaga cagtgcctag cgcaggccta tctctgccat    17580
ggactgccgg tagggcctca gtttccctat ctggaaatca agcagctgac cccaacagtg    17640
tcaccagtct tttcagggct gacattccag atttctaaaa gcccagaagt ctaagatacg    17700
gttatttgtt ccgagcctcc caggcgccaa gctctgggca gatttctggg gcaccctggg    17760
ggtcacgaga ccacacctgc cttctcccctg cctatccttg agcacagcca ggagtcgcgg    17820
```

```
tgccagaaac ggtggtccct gcagatgcca gtctagtctt cctgccaggg acgctagggg    17880
tcacagatga ttctgtagca gggtggaggg gtctggggag ggagcatggg actcgagcca    17940
gccgtcatca tcaaactgta agctccagaa gtctggggaa cctcctggcc tctctcaccc    18000
gaggagctag cctggtcctt ggagggcctt cagtctgtcc tctggggctg gggagacaca    18060
gaattctccc cacagacaca cagtggtctc tggtaggaga cccggaccca gaacccagat    18120
gtccagactc ccgtccaccc tcccccagca gccgcctgcc gccctccctg ccactcccct    18180
cccagacccc agcccagcct tgccacccttt ctgttctgcc agggtgtacg gctgcagccg    18240
ccaggagccc gtggtggagg ttctggcgtc ggggccatc atggcggtcg tctgaagaa     18300
gggcctgcac agctactacg accccttcgt gctctccgtg cagccggtgg tcttccaggg    18360
tgagaggtca ggggtccctg ggcagggga ggggtggtgg tagaatccaa gggccctcca    18420
ctgggctcac tgctcacctt ttttgcccaa attgaggatg ggatggggag agggaagatt    18480
ctggaagctc ctgctgctct ccactcccca ccccggcccc cctcttcctt ccgtcgtttg    18540
cacttccacc cccctcttcc ccttgaccgt cctaccattc gcagtctctg tcttcctggc    18600
atcgctccct tgcttccctc ctctttctct gtccttcctt ctctctcctt ttctcttttc    18660
tgtgctgacc gcctctcctc cctcctcact cgcctgacc tgtgtcccct cccctctgcc    18720
cctcaccccc tccctgccct ctcccttgg cacccaccgg tggctgggcc tggaacacgg    18780
gtctgtttgc agcaggacta agaactcctt ggattccgcc ctagacagtc cgcttacagc    18840
caagagggcg cagggagctt ggggaggtgt gatggcagca cagccaggcc atggccactg    18900
gtgtggcagg tctcccactg ccttcccagc ccccacccctc ctcctgcttc gggacctccc    18960
tccttgcccc cttcccagga agggcacgtc ccaccccgca tgggacagct gtcctgggcc    19020
tggaccagca atacttctgc gcaggaggcc caaactttgc catttctgga gctcaggagg    19080
ggaggatggc agagaggagg ccatagagtg ttggcagctg cttctgcctc acctctctcc    19140
ccactcttct ccctcccact cagggtccca gccctcttct cggtttatcc ccaaactgtc    19200
tggcatagac ctgggtcccc agctggccaa actggagcgc taaatgggta gcagagctgt    19260
tcccttggga gtctgacaca ggctcgaggc gggagggaac aaagggcttt gggggccctg    19320
gcccaatgga gagatggcca gggcaggtga gcatgctcct gtcctgaccc ctggacccct    19380
cagcctctca cggtgtagcc tcaaccaagc cactccttt ctccgaacct catcttggaa    19440
aaggggaaca gctctctctc ccccagccac caccgtgagg cctgtgcagg tgtgaatgca    19500
ttttgtaaac tggcgagtgc tgtcccgcaa atatcaataa ctaacacgga tcgagcactt    19560
actacatgcc aggctgtttg aatgtttatg tcttttaat ccactctact accctatgag    19620
gtgtgtgcta ttactgtcct cattttacag atgaggaaac tgagacccag attcacacaa    19680
tcacattcaa ccacagcaat ttgctggcag aggtggtagg ggtggtgggg ttacaagctg    19740
cgccagcctg ctgggaggtg cagccagggg acccctgtgt aacagctgct ctcctggtcc    19800
agcctgtgaa gtgaacctga cgctggacaa caggctcgac tcccagggcg tcctcagcac    19860
cccgtacttc cccagctact actcgcccca aacccactgc tcctggcacc tcacggtgag    19920
accccaccct gctgcccac ctgccctctg ccgcaagcac actacaggtc cctggtgacc    19980
cgggatgaga gggggcagtg tccgcctctc gctgaagcgc ccacaggctg agccctgggt    20040
acacatcctg ccagggtgga gagggctgtg ggcgaggtct ccctctgtgg gtcacagcaa    20100
tgcctgtttg ttgagtgact gacagacttt agccccacct gggattctgt gtttccttct    20160
cttttgttgtt agggaggtgg gttcaccaac ctggccacac cccatgggcc acctgatggc    20220
```

```
ccgctcctcc ctcccaggtg ccctctctgg actacggctt ggccctctgg tttgatgcct   20280
atgcactgag gaggcagaag tatgatttgc cgtgcaccca gggccagtgg acgatccaga   20340
acaggaggta ccacttcctc tcctccctct ggcttccttt cctccctccc cctccctctc   20400
ttccctcctc aatagtgacc ccctcattgg aagcccaagt ccccaatctc agaggggcag   20460
caaggggagc gagcagaggc tggggctggt gtcaggcctg ttgcccttga ccttgtcctc   20520
gtcccagcct ccgccctggc cccggcttcc cctctggcta cccagaggt ctcagacacg    20580 tttggtcatc agacaccttg gatgtttatt ctaattacag caaaattgtc tcatcttctt   20640
gggtgctgta accccctctg gcaccctcaa tccttcaata aaatgttttcc agagccaaag   20700 gactcatggg cactttggtg ccttccctct aaacccaagg cgtaccatca gaggtgcctc   20760
tcccttatca cgaaccccctg ctgcacagcc aggcccaatc ccattgcaca gggtaacatg  20820
gaaatcatgg gtgccctgga tcccccgaat ccccaacggg gcacttgccc tcttccctgc   20880
tcttgccctt gctccctctg gtaactaagt ttccgacaaa gaagtgagtc cttacagaga   20940
tgtgagcaag agacagtggg gttaggctaa gcgactaccg ttgccagggt cactatggca   21000
tgaggccagt aggtgcccac tgggcctggc caccaggaag ccatgggtgg tgccgacagc   21060
ttcagaggcc tgggctgggc aaggaggcag ggaaacagag acagggtgta tggacaggtt   21120
ttcatttgtc tgggaagaaa agagaactag gaaattcaag gaaggggaca tttaagacgg   21180
gagaggttcc atatctcaaa tgtgtggatc atcccagcat ccccagaggg agagaaggag   21240
gctcaggtgc aggtaatatt gtttagagtg gggaggggtgg gcaagggggag agggaggccc  21300 tcccatggct ccattgttgg ggagcagagg tttggggaga gagaagagga atattgaagc   21360
agcgatggca gagccaggga gacccttttcc ctgggaatcc ggggtgaaaa cggtcatcgt   21420
gtcagcgtca ggaaagagga gactctatcc ttcatcgcag gttgggcctc tgccctccct   21480
tccaacctcg gaattctggg ggcctaatgg gttcagagtc tagtatgaaa gatttgtcat   21540
ttcttgattt cacagagttt gaatatctaa gatgccagtc ttggaagatg ccaaaattgg   21600
aaggctctgg ggctctagaa ttcttggatt tctgggggtgt gtgttcccaa tcaccaacac   21660
ttgtaatttg cttgttggct gatcctattc aaaaggatca tccagacaaa aggtgacgaa   21720
gaatgacaag gtttgcttga ctccttttttg caatttatct gggactagga ttaaaagaaa   21780
ggagaagaaa tactcatggc atgatctagg gctatgctgt tgggggtaac atggggagtg   21840
actttgggcc tgtgctgttg ggggtgatat ggcgaagcag tgccttcagg gctttgcatt   21900
tggtggtgat atgctgatgg agtgtgacat caggcctgtg ctgctggggt gacatgctgg   21960
ttcagtgatg tcaggcctgt gctgtctgga gagcagaagg cttctgtagc atgatggggg   22020
cacctctggg aacggctgcc ctgaccccctc atggagctca cttgaagcct ccttgctact   22080
cacctaggct ggggatggct ggcttcaccc ccgctcacag gaacccgcag ggtgaccctg   22140
agatggatcc atgattcaca gttctgcgaa tgatgagaac atgttttcct gcctccctcc   22200
ctaccgcaga gctgaacttt atgtctcagg gaggcccaca aaggagaagg aacagtcttg   22260
ggtctgacac tccctgtctc atccctcacc cccttggcga ctccatttgc cagaggcggg   22320
gccccagcat tcaggggttg tgggggggttc ggtggcctgg agttaggtgc taagacaggc   22380
gttcagtgca ttggcccaac aacttgtgtg gtcattggcg ccgttcctgt ttcccagaga   22440
aggaaatcaa ggctcagcag gattaggtgg cacgcagatg ggtccacaga tggggtctct   22500 cccataccccc caacagccac aaacagcagg ccaaaggatg ctccacccca tgcttcctgt   22560
```

```
gggaaggccc tcctccctcc ctgatgcagt tgggcaaggg tctgggtact ggggagacag    22620
ggacttcgtg agctaccctt gggtaatgac agagagagtg tggaacacgg atgggagagt    22680
cttttcccta atccaaagga atgatgcctt gatggtgaat ttgaggcact aggacagctt    22740
ccaacagggt ggaggatct cgccagagtc tgagcaccac tgagctatag aatgtgtggg    22800
ctgaactggt cctagcaccc aacctatggt acaggtgggg aaactgggac cagcgagggc    22860
taaggacttg gcctcttgtc cctgtctttt ctgcctttca gtggtggaga tgggcttcag    22920
ggtgtagcca agcggtggct gggtggtgag gatgaggcct gacagctccc tgtgccccca    22980
tagctccccc tctctctgtt cagtcctccc tcgccacacg ggggtggaag tgctcagcag    23040
gggctggcat caggtttgc atggatccct agatgcaccc ccttccttgt ctgtgaaacg    23100
aggggttcag gccagcccag gccccaatc tttgattgct tacccatcag gaagctattg    23160
tctcccatac aagttgtgtt tattaattcc tggccaaacg ccattccaag tcaggctggt    23220
gaggtggaaa gcgcttaagt gtcgaagcca gacaggccag ggctcagcac ctgtctcctc    23280
tgcttcctac ctgggcgagg acttacatct cccaacctca ggtaactcat ctgaaaaaag    23340
ggcgtgaaag agaccccac cctgggaaga ctaagtgaga caacgcgtgg agaacattgc    23400
acacgcgggc ttaggtcaag tgcaacaaac ctgcgttcat caccggctct cactctgctc    23460
tgggcaggca aagctgagg ggtttatggt gctggctctt tcagcctcaa caacccagcg    23520
aggaagcagg tgcctgtact gccttcacag accagtgaga cacccaagac acagagagat    23580
gaagtaattt gcacaaagtc acccagctct ttgagccaga gttaaggcca ggcagcctga    23640
tctggagtgc acgtgggtgc acagatgcat gtctgtgtgc gtgcgtacat ccatgcatgt    23700
ctgtgcacgt gtacgtgcat gtgtgtgtgg tccacgtgtg cgattcttcc ctctgagcct    23760
ctagcggccc atgccagctg gtgactccct cagccaaggc atcccagcc aacccactgg    23820
catctgggtg gggggatcga cagtttctgt ggctgtccca ccagttccag agcggcctgg    23880
gaagtcccag cccttcttc tcagactttc attaagggtc cagggtcccc aggggcagac    23940
tcttgtcccc tccccgcaga ctcctcctgt gtgaatgaat gtggaaggga aggcagaggt    24000
ggcgcctgca aaccatccgc actgggccac tgtgccctct agttatgatc atgggcgata    24060
gtgatcatcc catgtagatg ctgagaaatt cttagaatga gcatttgttg gaaatctgct    24120
tgtgtgggtg gcaaagacat gagaggtcta gggaagagca gattttcaga caaggcactt    24180
tagggaggggg gaggtacagc cctttggccc agaatgccca ttgatggaga gggcgggtca    24240
ggggagaggg tatcttaacc ctcaagtgcc agcgtagtga tgaggaaagg ctggcctggt    24300
gggccccca tggactaagc atccttaggc acttcacctg actcctctga gactgtggtg    24360
cctccttcac ccctgacctg cctgctttct acctagcttc tcccggtgcc cacttgagcc    24420
cagctgaggc ctcaggccct tgagtggcct gggggtggta gagggacttg gcccgtgaga    24480
tctggccatg gctgctccat ttcgcagaag ccactctcac gggctgccac cgaagcacgg    24540
gcttcccct ttccgggaac ctgcctcctg ccagcttcct ctcctgtgac atcacttctc    24600
ttgtgattcg ccccaccatt tccactcact cccagccagt ggggacaggc agaaccatgg    24660
gttccctagg ccagctggag ccaccccga cccggcctgg cctggctatg gggtggccct    24720
tgtgttctcc ggagcgctag tggccagcac aggcggcagc cacagacact tagtaggaac    24780
ttcagtgtgg ctgacctgag ctgggctggc cgtgcaggag agtgcaagct gcttcctcca    24840
tgagctcaca gcctgacgtc agcaagtgct tcaaagaagt catttcctat gcatgcctta    24900
aaccatgcca aagggagat acgatcaccc ctgttttaca aatgtgaaaa ctaaagcttg    24960
```

```
ctgagggtga cccaaggtca cacagcttgt tcctggggca aagccaggct gccaattcag    25020
ctctgcagcc ccaggtctag agctctggca atgccaggtg ctgctctcct ccctcttca    25080 gcacttgcct tctgtgaccc tccttcccct ttaatctgtc tgtaggtaag ggcacggggg    25140
tgtgcattca tccacccacg cacccttctt tccttcttcc ttcttgtgtt ctccccaccc    25200
ttccatccat ccatccatcc atccatgcat ctatccctcc aggcagtaca tcctgacagg    25260
gtccctgtct acctcctgga tgaggcaaga aggaaatatt ccccatatcc agagaggtga    25320
ggaagcaagg caggccacac ggtgcaaaaa tgtgccttca gacactcagt actttgtagc    25380
caagatgaac tggcaggcat cgcagcagtc aggcttctgg tgcttcttgg agagggctag    25440
aggggagcac ttgttggacg ggaggcactg gagagccaga gaatgtgcac cctcccccag    25500
agagttctgc agcagaaaca gaaaactcag atgggccaag gggccaggcc agggctagag    25560
tctatgatgg ggggtagggt agtccagtgg tgttttcggg gcttttcttt ctttctctct    25620
ttctctttct ttctttcttt ctttcttct ttctttcttt ctttcttttt ctttcttct    25680 ttctcttttt ctccttctcc ttctccttct tcctcttctt tctctttctt ctttcttctt    25740
ccttattctc ctttttcctt cttctccctt cctcttctcc ttcttctcct tctcttcctt    25800
ctcctcctcc tctttcttct tctctccctt ctcctcttcc tcctcctcct tcttcttctc    25860
ctcctccttc tcctcattct ctttctcctt tcttcctctt catcttttct tcttcttctc    25920
ctccgcctcc tccttcctct tcctcttcct cttcctcttc tccttctaaa ggagcaggaa    25980
tctggattat tatgtgaaat tagctcgcga ctcaatgaag caatttctac atggtgcata    26040
aacagattgt ctttacgctg agtgactccg cttgggccac tagatttcag ccgctgcctt    26100
gaattcctct ctggcgcttt ctaagcagac gcttgttcca gggattccac cacctctacc    26160
cgtgctccag gcctccagag tgagaaccaa acactgccca gacagacagg ttcccgggta    26220
cacggtgagg ccctggggaa aggttgctgc cagctacaga ctggttctag gactctccct    26280
ggaggttgag agaacttcct gtagcaggca caggtgtctt tgccttacag cccctgccca    26340
aggcttgggt gacactacag gtcctcaacg cagttgcttc tagggtgaaa cgttccactc    26400
ccctccaacc ccggcttggg ttccttctct gtctccccac aatctccctg tgactgtggg    26460
aagggacacc ccaaggccca tgggatgcgc ttgactcctc attccccgca ctagtccttc    26520
ccaacccctg gctcccctgt ctacttcctg aggtccttct gtgaggaaaa caatccgatga    26580 taactttata gacaaacaga caccaaaacc tgcgtttcct gggttttaca agagcaagag    26640
ggccaggctt gctcagggc gcccctggc ggtgcctcgt cccccaccgg ccctgctggg    26700 ctggggaac catggtcggg ggtggcggct cccaacctgt tctgcctcag gacccagtca    26760
ctctccgcaa aatgactgag taccctaaag agttttgct tatacaggtt atagatctat    26820
acttgcagca ttagaaattg aaacaaaatt ttaaaatgtt tattaattct tttaatataa    26880
ttataagccc attacacatt tgaatataaa taacattcta tgaaaattag ttgcatcctc    26940
caaaagtaaa aacatttagt gacaagagtg ctgtcatttt acatttttgt acatttcttt    27000
aacaactggc ttcacagact acaggcggga ccttcgaatc tgcctccgag ttcaatcagt    27060
cccgatgtca cacatcagtc tctgaaaaac tcgcctgtca ccttatgaga gaatgagggc    27120
aaaaaaggca aatgatatct gagtgttact ataaacatga cttttggacc cccagggtc    27180 ccctgactgt gctttgagaa ctgctggttg gtgtaagggt aagatcgtgg tcactgtggc    27240
cagatagact taggggggtg ccagagtcta ggccaggcgt gtggaggaca tggggcatgt    27300
```

```
aggggggctca gacctcagag ctcctgttgc agtgggaatt cggagccctc ccctcaagca    27360
agctaggtga gctcttctgg gtcctgaggc aagattctgg ctccaccttg gctcctgcac    27420
tcttgagcct catctgtaaa atgggatgag agcaattcct ccctccctgg gtggaggtgc    27480
tgcttgaacc tcagaatccc cgtgcaatga ggccttgtga tgccatagcc aatgaggctc    27540
agccccagcc acacacctgg agatgttaaa acagcctcaa agctcatctt cagctgttcg    27600
gtggctaagg aattgattaa cttattgaac ggttaagtgc ttaccacatt ctagaagttc    27660
tggggaagtg cctggcccct gggaatcatg gccggctccg cagggtgttg gatttgctgt    27720
gggatgtccc cactggcctt caggggcatt cctgatgctc tctggatttc catctgcttt    27780
ctctgccagg ggcattttca gctctccctg cagattttca acctgcaccc tgagtgtgtt    27840
tcccccatct gcaaagcact ctgatttgct ctgtggaggg catttctatg agctgatgaa    27900
gctgtcccca tctgttctgc aagggtgtcc cacctgggat gaaaaggaac ccccggctgc    27960
tgtggaggga gggtcccact gtcctggggg agtggctgca cccactctgt gaagtcatgc    28020
cgctgcccac ttgctctgtg gggtgaggtg caccggactc tctgcaggag gaaccccctgg    28080 gcccatgccc tggagatggg agggctccta cctgttctct ggtaggagag aaagactcag    28140
cctctctgga gattccccca cctgctctgt ttgaacaacg gtatcttctt ggtggtggta    28200
tggcaggggt gcaggggcgg tgttgtccag cagggatgtg agggtgctcc cacagctggg    28260
ggtggtccca ccccgtgtgg ccatgcacag agaaggtgct gcccatcagc actaagctac    28320
tggtcatggg agaaggactg gtccttccct caagcccaca gtgtcacagg gaggcaggag    28380
ggttggtgcc taaatgggga gcactgctgc cccctcgtcc cacaccaagc tcaaggcaga    28440
tgaccgtgca catctgtgga cagtggggca gtcaagggct tttgcctcaa ctgacacatt    28500
gaagcctttt gtcagattca agatcaacag aaataatttt tcctttcttt ctttctcttt    28560 cttcttttc ttttctttt tctttccctc cctctctccc tttctttctt tctctttctc    28620
tttcttcttt cttttcttct tccttcttt ctctttcttt cttcttttt ccctccctcc    28680 cttccttcct tctttccctc cctccttcct tcctaccttc tgtctctttc tttctttttt    28740
tgacgtactt tcgttcttat tgcccaggct ggagtgcaat ggcacgatct cggctcaccg    28800
caacctctgc ttcctgggtt caagcgattc tcctgcttca gcctcccgag tagctgggat    28860
tacaagcatg tgccaccatg cctggctaat tttgtatttt tagtagcaac ggggtttctc    28920
catgttggtc agtctggtct cgaactcccg acttcaggtg atccacccac ctcagcctcc    28980
caaagtgctg ggattatagg tgtgagccac tgcgcccagc caattttttct tgttttataa    29040 gggaggaagg tgaggctcaa agaaggaccc tgacttgcta gaacctcaca gttcacaggt    29100
gactgtgact agaattgagt tttttatctg gcaggcaatg gggagccatt gaagattttt    29160
gagcagggca gtggcatagc caggctagtt tctagaagat gactctgggg gtgcactcat    29220
ctaagggaga aatcagggca gaggaggcac agcgggcgtg cagctccccc tgcccctctg    29280
gctgcctgtc cttgctctgt ctgtgcacgg gacccaggag accagccagt gcagccctga    29340
gtcgtctctg actccccca ggctgtgtgg cttgcgcatc ctgcagccct acgccgagag    29400 gatcccgtg gtgccacgg ccgggatcac catcaacttc acctcccaga tctccctcac    29460
cgggcccggt gtgcgggtgc actatggctt gtacaaccag tcggaccgtg agtatgggca    29520
gccgggggaa cccccctgcag tgactcgctg cctcttggcc atccctggaa ccaccaaggg    29580
ggctgtgggc agctgcttat gaggctgaac aaaaggagag agagagtgtg tgtgtgtgtg    29640
tatgtgcttg cacaaattta tgcagctttg tgtgcccacg tgtgcaaggc agccacaagg    29700
```

```
gtttgcagga atacacactc atacatatcc acgtgtgtgt tgtgtattct gtgtgtgtgt  29760
ctggatatgt atgtctgctt ggactgtgta cacaggtgcc caggaccacg tctgtgggtg  29820
cctgtccatg cgcgtgtgag tgaacaggtg catgcgtgtc tttgtgcgcc ttcgcggcta  29880
cgcatggcct aatggcgccc tgcctgcctc cacggtcccc tgtggttttg cagcctgccc  29940
tggagagttc ctctgttctg tgaatggact ctgtgtccct gcctgtgatg gggtcaagga  30000
ctgccccaac ggcctggatg agagaaactg cggtgagtaa cccgcccgcg catccctcct  30060
ctccctgccc atcccttctc cttcctcacc tttcctgctc tgagctgagt ggagacccca  30120
cttctacatg cagcttccat tatgagcacc caggaagtgg ggttctctca ctgtgccggg  30180
gtggcaaaat gagacagacc agcaatgcag cctccccgag accacctcgt gggacagtgg  30240
cagggagaag tggggagcca ggtctcctga cttccagctc agggccatca cccccagccc  30300
ctgtcccagc cagccttcca ggaaggaaca gaatgggtga gggagatgtc cccctcctct  30360
gccctgtcaa aggtttaaat atgtgggaag agggaagcga gatgttcatg gtgggggat   30420 gatcctgcca cggtgctggg ggaggtacct catattcaga aactgaacat ctggcttcaa  30480
gttctggctc agccaagtga ccttggacaa gtcacctcat ctgtttccac cagtgaaatg  30540
gggtatctca cagggttgct gtgaaacttt gggtgtaaaa tagcagagaa agaggccggg  30600
cgcagtggct catgcctgta atcctagcac tttgggaggc ggagtcgagc ggatcacctg  30660
aggtcaggag ttcaagatca gcctggccaa catggtgaaa ccccgtctct actaaaaata  30720
caataattag ctgggcgtgg tagcaggagc ctgtaattaa tctcagctac tcgggagtct  30780
gaggcaggag aatcgcttgg acctggggagg ttgcagtgag atcatgccat cgcactccag  30840
ccttcgtgac aagagcgaga cataaaaata aagtagcaga gaaagagatt tgtgattggt  30900
aacgtgcaat acagcacacc ttctacaggc atcgccaagc cccggctggc tcctctggct  30960
tcctcccacc tgtcccctct ctgtgtcccc acacagtttg cagagccaca ttccagtgca  31020
aagaggacag cacatgcatc tcactgccca aggtctgtga tgggcagcct gattgtctca  31080
acggcagcga cgaagagcag tgccaggaag gtagggcagg cctagccgag tgtctggagg  31140
gacaccaaag gcagtctagg cctgctacat gcttcagcaa aagtttctag cttctcctct  31200
caacacccac caacccctct gtatttacat ctgtatgtct gtccattcat ccatccatcc  31260
atccatccat ccatccatcc atccatccat cctcttctg gtctccaatc accgtctgtc  31320
cattgattca tacagctacc catttatcta tgcatctact gacctgtgca accatcaatc  31380
tccctatcat caaactgtca atctacccat ttattggttt ggctgactac tggtctatat  31440
ggccactgtt ccatccatcc atccatccat ccatccatcc acccacccat ctacccaccc  31500
acccatccac ccatccatca tccatccgtc catcatccat ccatccatca tccgtctatc  31560
catccatcca tccatccatc atccatccat ccacccatcg tccatccgtc catcatccat  31620
ccatccatcc atcatccatc catcatccat ctatccatcc atcatccttc cacccatccg  31680
tcatccaccc atcgatcatc catctgtcca tcatccatcc atacatcatc catctatcca  31740
tccatccatt catccatcca tcatccatgc atcatccatc catcatccat ccatccatcc  31800
atcatccgtc tatccatcca tccatcatcc atccatccat ccatcatcca tccgtccatc  31860
atccatccat ccatcatcca tctatccatc catccatccg tccatcatcc atccatccat  31920
catccatcca tcatccatcc gtccatcacc catccatcca tcatccatcc atccatcatc  31980
catccatcca tcatccatcc gtccatcatc catccatcca tcgtccatca tccatccatc  32040
```

-continued

```
catccatcat ccatccatcc atcatccatc catccatcca tcatccatcc attcatccat    32100
catccatcca ttcatccatc atccatctgt ccatcgtcta tccatccatc atccatcatc    32160
catccatcca tccatccatc catccatcat ccatccatcc atcatccatc aatccatcaa    32220
tccatcatcc atccatccat catccatcga tccatcatcc atccatccat gcacccatcc    32280
atcatccatc catccatcca tcatccatcc attcatccat catccatcca tccatcatcc    32340
atccatccat catccatcca tccatgcaac catccatcat ccatccatcc atcatccatc    32400
catccatcat ccatccatcc atccatcatc catccatcca ttcatccatc atccatccat    32460
ccatcatccg ttcatccatc atccatccat tcacccatca tccatccatc catcatccat    32520
ccatcatccg tccatccatc atctgtccat catccatcca tccatcatcc atccaaccat    32580
ccatcatcca tccatccacc atccatccat tcatccgtca gccatccatc catccatgca    32640
cccatccatc atccatccat ccatccatcc atcatccatc catcatccat ccatcatcca    32700
cccatccatc atccatccat ccatctaccc atccatccac ccatccatcc acccatccac    32760
tgatctccct agccccctgt ctgtccactg gtccttatat ccacacgttt atccaacctt    32820
ctagctgtct gtcagtctcc ctaatggacc accactccac ccattggctt gtctgctcag    32880
tcttctgtct gggtctattt atccatccat ccatctaccc atccaactga ccaactgacc    32940
aacacttgca ggctacccag cgataggcaa ggtgcagtaa ggaagtgaga ataaaacagc    33000
agagatgcag gccctgcctt ccaaggctca tctgttagta ggaggatatg atgggtgact    33060
ctcctgcctt gtaggaagat tggagggcag ggaggaggtc agacatgaaa agcttcctgg    33120
aggaggtagg tgtttggccc ttggtgagag ctaaaactta aataggcagg aggaaaggag    33180
agaggcaaag accaagtggt ggagtggaaa gttctttaca gtgaagagca gggaggaaaa    33240
tgtggacaac cgggcagggc cagagcctgg gagattgcca ggctaggtgc ggaccctggt    33300
ctaaaagtgg aggcacagtt ctgccttcaa gttccacact ggaggggag gcatgatctt     33360 gtggtcagga tctccagtct gagaatggag acaccacttt gtgctcaata ggccagtctg    33420
agtggagggg ctgtgggggg cgggggaca tggcctgctt ttaggagacc ctaaaggaga     33480
ctcaggaaaa gactctctag tcacctcctg gctcttctgg ctccatcgtt cctgcaccc     33540 actttggaag gtttccttgg ggctcagaga cccaccttct gtgccctgcc cccatcccct    33600
ctgtcccagg ggtgccatgt gggacattca ccttccagtg tgaggaccgg agctgcgtga    33660
agaagcccaa cccgcagtgt gatgggcggc ccgactgcag ggacggctcg gatgaggagc    33720
actgtggtga gccctgcctg gctgccgggg ccctggagct tgggagggag ggggtgccca    33780
cagcaggaag ctggagggaa atctcactgt tgtcccctgg tctctctcta tctcatcctc    33840 tgccccttg cctgggtcct gatggtctct ccccctccat cattctcctg ttctctgtct     33900
ctccatctct ttcctttgcc cttcctctct gtctgcttct ccccttcccc tcctcctctg    33960
tccaccccac cacctgcccc catccccaga ctgtggcctc cagggcccct ccagccgcat    34020
tgttggtgga gctgtgtcct ccgagggtga gtggccatgg caggccagcc tccaggttcg    34080
gggtcgacac atctgtgggg gggccctcat cgctgaccgc tgggtgataa cagctgccca    34140
ctgcttccag gaggacaggt gagcgggagg gtgtgggggc ctaggcagta agagacaagg    34200
gcagggaagg cccggtggga ggtgcactgt gtctgagctc tttgcagata gagggaaggg    34260
tggtggaccc cccagacagg ctactgtgat gtgagttcta gtcctggctc caccaggacc    34320
ttctgggtcc ccggacacat tgttccacct ctctgccatc tacttttggt atcttgcttt    34380
aagttgggcc agtaattcat tcattcatct cattcactca ttcagcaaca cttgtgctcc    34440
```

```
tactatgtgc cagggctgtg ctagatgctg gggattcagt aaaggacaga actgcccaac   34500
ctggtcataa gctatgacac tccccgaggt gtgacacgag gtagcaggtg gggctgggga   34560
gcccccaggg gacatctcat caggcctcat ggccatcttt cccatctgct tggtgggctg   34620
aaacctcccc caatccaccc ccagacagat ctgggctcca gatcccgccc caggccctg    34680 cacagggatc ccctttttgta tcctctctgg gacgcagggc gctctgacca cctagctctc  34740
tttaacccca tctcaggctc cccactgccc tcaggtagag ggtagagacc cgaaggctgc   34800
ccatctgcca cccaggcagc tgactgccgc agtccaattc ctccacgctc aactcccacc   34860
cgctccccac taggacccac cagcctcagg gaattcagag cagcctgggt ctgtaaagca   34920
cacaggaaaa aagaaatctg tgtcgggggc ctggcactgt gctacatttt ttagatacac   34980
ggtcttattg gattctctca agaacattcg agtagaaaat gccattccca tttgcagatg   35040
aggtggcaga ggcttagaga ggcacaccca tgtctaggga gggatgaagc tggggcgtgg   35100
aacccaggca ggccgagtgg gtgaaggctg aacgctgtac caccagctag gcgaccttca   35160
gggagggaag ggagggctgg gtgtggaggg cactgtcccg ggcgggatc tggctatctt    35220 gagggtccct ggatggggag aggcagcttc ctcccacctc acctcacccc accccacccc   35280
accccacccc accccagcat ggcctccacg gtgctgtgga ccgtgttcct gggcaaggtg   35340
tggcagaact cgcgctggcc tggagaggtg tccttcaagg tgagccgcct gctcctgcac   35400
ccgtaccacg aagaggacag ccatgactac gacgtggcgc tgctgcagct cgaccacccg   35460
gtggtgcgct cggccgccgt gcgccccgtc tgcctgcccg cgcgctccca cttcttcgag   35520
cccggcctgc actgctggat tacgggctgg ggcgccttgc gcgagggcgg tgagcagcgg   35580
ggacttgcgg cgggaggcgg agggagaccg tgcggatctg cgccgtaaca cctggcctgg   35640
agaagggcgg ggctgggggt cccggggctc cacccccatag gccctctagt gctgggattc   35700
aaattgggct gaattttacg gtagaaaacc accatttaat gcggcctgta ggcccctgcc   35760
cctcccctcc tagctcttcc cttccttctg gaagggcgtt atgtgtgggg caaaggggca   35820
ggtctgggac gccactgccc acgtgcaagc tccacctgct gttccttggg ctgcaagggt   35880
ggaaggctct taattactag cactttccac atccaggctg gattttaggg gaacttgact   35940
tcatataatc cacccaacag ccctacgggc ggatgctgtg gccctatttt atggatggag   36000
aaaccaaggc tcagagacat gttgctgtaa gtcacacagc cagagaggac tggagcaaag   36060
attagaaccc agggctggct gcctccagag cccctgctct tcctgctact gctctcagaa   36120
acagggtctc tccccttct acgttcactg accagagtcc ctgcggcca ccgcacagtt     36180 ttggggacac agaccagct ggcaaaccta cagacatgcc ctgcagcgtt agtgttggtg    36240
gcttcaaaaa tgtgtacagt gacttacaat ctggaagcag gcggggccgc agagatattt   36300
taaggatggg gaaactgagg ctcagaggaa cagtgactta cccaagggga tggcagtggt   36360
catggcaaag caaggctggg ttcattcact attccttcac tcattcagtc actcaatgac   36420
actttctgag caccaagtac gtaccaggcg tggggttagg ggaagggtac ataaggatga   36480
agagagaaca ttctcggggg agacagacag tggtaagagc tgacatggat ggggagatgc   36540
aggaacagtg gagacacaga ggaggctcct gcccagctag ggtcagggga ggcttccagg   36600
ggagggttgt ttaagctgag gcctggaaga tgagttggca acattcagac aaaggggaaa   36660
gacattcagg tgaagacaca ggtgccaaga caggaagatg tgagaacatc cgcagcctgc   36720
cagaggggct gaggtggggg gcaggcgtgc ctgggcgagg agcaaccaga atggcagaca   36780
```

```
gggccttggg cgaggagcaa ccagaatggc agacagggcc ttgccggcca gcataaggat   36840
cttaggccag gagttctccc tcctacctgc accttagaac catacgggga gtttcaagaa   36900
aaactgcgta tcaaggctcc ccgggggact gtgatatgca gccctcgtgg agaagcgcta   36960
gggcagactg cagagttggg gcactgcaga gttctaagga aaccatgaag ggatcagatg   37020
tgggcttcgg agacatctgc aggtgctgta acagagcagc gaggagccag ccagagccca   37080
gaggtgcctc agcagacaga ggtgggggac aagaagctgg aggaagacac tcatccacac   37140
gggcttttt cttttttctt ttttttgttt ttttgagaca gagtttcgct cttgttgccc    37200
aggctggagt gcaatggcgc gatctcggct cggatccccc tcctcccggg ttcaagcggt   37260
tctcctgcct cagcctcctg agtaactggg attacaggca tgtgccacca cacccagcta   37320
attttgtatt tttagtacag acagggtttc tccatgttgg tcaagctggt ctcaaactct   37380
tgacctcagg tgttccgtcc gcctcagcct cccaaagtgc tgggattaca ggcatgagcc   37440
accgtgcccg gccctccaca tgggcttttgg tcggggggctg tcaccatgaa ccccacagag   37500
aaagagctag aataaagtga cagggaggca gaggggcagg tgcgaccccta gcaggggtaa   37560
gggtgggcag agcaggagag aagtaggctc ctgagatgca aagggaataa tgttagggag   37620
aatagagaac aggggctcca ggctcctgag atctcacttc tgcccttgac cacggacagg   37680
ccccatcagc aacgctctgc agaaagtgga tgtgcagttg atcccacagg acctgtgcag   37740
cgaggtctat cgctaccagg tgacgccacg catgctgtgt gccggctacc gcaagggcaa   37800
gaaggatgcc tgtcaggtga gtccccggg catgggaggg agagaggagg gagaaaggat    37860
gctgcccaca tcaccagggt ctggcccttt gctcacatca gcctgctgaa gcctcccatc   37920
ctcccagcaa ggtggtgatg gccaccccta ctttacagaa gaggagactg gggcttagaa   37980
aggttgagga gcttgcccaa ggttgcagag ccacagatca aagagatgc tgtgatggc    38040
aggtgttagg ctcaaaccca gttctgctcc ttgcccacca caaggcacta ggcccagggt   38100
cccacagtga ggtggatgca tggaagaaga aaggggtgtc agccacagaa gggaggcgga   38160
ggcagagtgg gggcgtgggg acacagccac agttccagga ggtcccaggc tggctggagg   38220
ccggggaggg ctggcttggg ctctctccat ttagcaggcg aggggaaagc agagctttaa   38280
gactgaacgt gactctggca cccagtcaat tcccaacagt caggacttaa tccctatggc   38340
tcttcacctg gaaaaggggg tgcccttacc ctgcttcagt cctttctcct ttccccctttt    38400
cagggtgact caggtggtcc gctggtgtgc aaggcactca gtggccgctg gttcctggcg   38460
gggctggtca gctggggcct gggctgtggc cggcctaact acttcggcgt ctacacccgc   38520
atcacaggtg tgatcagctg gatccagcaa gtggtgacct gaggaactgc cccctgcaa    38580
agcagggccc acctcctgga ctcagagagc ccagggcaac tgccaagcag ggggacaagt   38640
attctggcgg ggggtggggg agagagcagg ccctgtggtg gcaggaggtg gcatcttgtc   38700
tcgtccctga tgtctgctcc agtgatggca ggaggatgga gaagtgccag cagctggggg   38760
tcaagacgtc ccctgaggac ccaggcccac acccagccct tctgcctccc aattctctct   38820
cctccgtccc cttcctccac tgctgcctaa tgcaaggcag tggctcagca gcaagaatgc   38880
tggttctaca tcccgaggag tgtctgaggt gcgccccact ctgtacagag gctgtttggg   38940
cagccttgcc tccagagagc agattccagc ttcggaagcc cctggtctaa cttgggatct   39000
gggaatggaa ggtgctccca tcggagggga ccctcagagc cctggagact gccaggtggg   39060
cctgctgcca ctgtaagcca aaaggtgggg aagtcctgac tccagggtcc ttgccccacc   39120
cctgcctgcc acctgggccc tcacagccca gaccctcact gggaggtgag ctcagctgcc   39180
```

```
ctttggaata aagctgcctg atccaagccc cgctgctgga gtttgaatgg gacccaggca    39240
ccagcctcat gcccttgact ggagcagccc ctgcttcctg ctcagcctgt ttgacaagtg    39300
tccagaaggc caaggtgggc tcagtggcag tgggcgtggc cactgagggc tggggcctgc    39360
agggcagctg cccaggtccc agaagaaatg ccaggaaggc aatcatttgg ggaccctcag    39420
gtcagaggga tgtgaggagc aatcgtctcc ttttggaacc ttaggaggaa actgaggctc    39480
agagaggcgg ttaagacatc ctcatagtgg cactgggggt taggagtgga ggtggcatag    39540
actcctgtct cccagctccc tgtctgccaa ggccccgtcc agtgcgacac tcccttcctt    39600
tgcattcttt gagccactga ataaagcctt gggctccaac catgtgccag cactatgctg    39660
gggccacagg ggtgaaggac ctggctcctg accccaggag cagtggggat gatccagtgg    39720
gaaggggccg gaggggagcg tggactgggc aagtcaaggc aagctgcctg gaggctgtga    39780
gacttgagct ggggttcaga ggtggtccag gtgggaatat ccgggaagga tattccaggc    39840
agggaagagc acgtgcaaag gcacagtccc ggaagaatga ggcacgctag gacccagcaa    39900
gccgagtgag tgttagaaca gagctcgaga ggatgactca agaattcaga ggggcgaact    39960
gaggcgggat agcagagcct gggggttgagc caaggatttg atcttgaaag ctctggggag    40020
ccacggtggg ctctatagca taggagtgac atgagaggat tcacattttg gaaccagcct    40080
tggcaccagt gtgcagggag cggcaggcag ggaggctggt taggaggcca ccgcaggatt    40140
ccaggatgga gaggatgggc cgggactgag cagcgccatg ggatggactg gaggatgatt    40200
ttagacccct gggggcagtt tgatggagg caggggctc gctggaggtg agggtggacg    40260
gtcaagtgtg gacaactctt tctagacgcc taactgggag cggaagggag agagggagct    40320
tcagaggggc cccagactga agaggggttt ttccaacatg ggcgctgctg ccaggtctgt    40380
gggtgaatga ggcagaaggg gaaccaggga cggggagcac ccacctgggt cctgccagga    40440
cgagccggag cagctgggtg ggcagggagc gtctccagag caggtgggca gaacacatgc    40500
agaataccct gggtgatctg gaatcaccct gggccctacc tcagtcttca tcggaatcct    40560
ggagggcggg ggacgtgtca tctgttctcc taacaagcct cctggtgact cttttgcaag    40620
gatagttgga ccctaaaaat gagtccagct ttggagtgga gtgtcctcag gggaagtggc    40680
gaggccctcc aggcttgagc tggcaagagg gtgcccccgc ccagcctgt ggaaggcctg    40740 cgccttaggg gctcactgcc cggcaggatt tcctcgagca gcggggagga ctgaggagtt    40800
gaaggaactg gccagggtgg gtggagggtc tggggtctgg gctgggtcca gcagggtcag    40860
agaagggaga gggcggggtg tttatatttc ctaggatttt gggcagaggg gtggcagcaa    40920 tagggagggga tggcggtggc ccaggtgtca gagtagaagt ggagggggcg cgctgagagg    40980
tttaggatgt ggcagaggca gcccagggct ctccctagag ttctgttttc tggctcccgg    41040
ccaggtaggg caggtgctct ggtatccggc cccagggcaa aggatatagc cagttcccca    41100
agccctccct gcaacacaca caggaaaatg acaacagggc agcgtccctg ggcttttggg    41160
acaaagccgc gttcctttgg accagactac cacaccttta gtttagcccc gtccccaaaa    41220
gtggcccaga gaaagagggc aacagccagg c                                  41251
```

<210> SEQ ID NO 4
<211> LENGTH: 2691
<212> TYPE: DNA
<213> ORGANISM: Homo sapiens

<400> SEQUENCE: 4

| | |
|---|---|
| ggacaaacag aggctcctga ggcctgtgtg caggcccggc acctatctgc cactcccaaa | 60 |
| ggatgcccgt ggccgaggcc ccccaggtgg ctggcgggca gggggacgga ggtgatggcg | 120 |
| aggaagcgga gccagagggg atgttcaagg cctgtgagga ctccaagaga aaagcccggg | 180 |
| gctacctccg cctggtgccc ctgtttgtgc tgctggccct gctcgtgctg gcttcggcgg | 240 |
| gggtgctact ctggtatttc ctagggtaca aggcggaggt gatggtcagc caggtgtact | 300 |
| caggcagtct gcgtgtactc aatcgccact tctcccagga tcttacccgc cgggaatcta | 360 |
| gtgccttccg cagtgaaacc gccaaagccc agaagatgct caaggagctc atcaccagca | 420 |
| cccgcctggg aacttactac aactccagct ccgtctattc ctttggggag gaccccctca | 480 |
| cctgcttctt ctggttcatt ctccaaatcc ccgagcaccg ccggctgatg ctgagccccg | 540 |
| aggtggtgca ggcactgctg gtggaggagc tgctgtccac agtcaacagc tcggctgccg | 600 |
| tcccctacag ggccgagtac gaagtggacc ccgagggcct agtgatcctg aagccagtg | 660 |
| tgaaagacat agctgcattg aattccacgc tgggttgtta ccgctacagc tacgtgggcc | 720 |
| agggccaggt cctccggctg aaggggcctg accacctggc tccagctgc ctgtggcacc | 780 |
| tgcagggccc caaggacctc atgctcaaac tccggctgga gtggacgctg gcagagtgcc | 840 |
| gggaccgact ggccatgtat gacgtggccg ggcccctgga agaggctc atcacctcgg | 900 |
| tgtacggctg cagccgccag gagcccgtgg tggaggttct ggcgtcgggg gccatcatgg | 960 |
| cggtcgtctg gaagaagggc ctgcacagct actacgaccc cttcgtgctc tccgtgcagc | 1020 |
| cggtggtctt ccaggcctgt gaagtgaacc tgacgctgga caacaggctc gactcccagg | 1080 |
| gcgtcctcag caccccgtac ttccccagct actactcgcc ccaaacccac tgctcctggc | 1140 |
| acctcacggt gccctctctg gactacggct tggccctctg gtttgatgcc tatgcactga | 1200 |
| ggaggcagaa gtatgatttg ccgtgcaccc agggccagtg gacgatccag aacaggaggc | 1260 |
| tgtgtggctt gcgcatcctg cagccctacg ccgagaggat cccgtggtg gccacggccg | 1320 |
| ggatcaccat caacttcacc tcccagatct ccctcaccgg gccgtgtg cgggtgcact | 1380 |
| atggcttgta caaccagtcg gacccctgcc ctggagagtt cctctgttct gtgaatggac | 1440 |
| tctgtgtccc tgcctgtgat ggggtcaagg actgccccaa cggcctggat gagagaaact | 1500 |
| gcgtttgcag agccacattc cagtgcaaag aggacagcac atgcatctca ctgcccaagg | 1560 |
| tctgtgatgg gcagcctgat tgtctcaacg gcagcgacga agagcagtgc caggaagggg | 1620 |
| tgccatgtgg gacattcacc ttccagtgtg aggaccggag ctgcgtgaag aagcccaacc | 1680 |
| cgcagtgtga tggcggccc gactgcaggg acggctcgga tgaggagcac tgtgactgtg | 1740 |
| gcctccaggg cccctccagc cgcattgttg gtggagctgt gtcctccgag ggtgagtggc | 1800 |
| catggcaggc cagcctccag gttcggggtc gacacatctg tggggggcc ctcatcgctg | 1860 |
| accgctgggt gataacagct gcccactgct tccaggagga cagcatggcc tccacggtgc | 1920 |
| tgtgaccgt gttcctgggc aaggtgtggc agaactcgcg ctggcctgga gaggtgtcct | 1980 |
| tcaaggtgag ccgcctgctc ctgcacccgt accacgaaga ggacagccat gactacgacg | 2040 |
| tggcgctgct gcagctcgac caccggtgg tgcgctcggc cgccgtgcgc cccgtctgcc | 2100 |
| tgcccgcgcg ctcccacttc ttcgagcccg gcctgcactg ctggattacg gctggggcg | 2160 |
| ccttgcgcga gggcgcccta cgggcggatg ctgtggccct attttatgga tggagaaacc | 2220 |
| aaggctcaga gacatgttgc tgccccatca gcaacgctct gcagaaagtg gatgtgcagt | 2280 |
| tgatcccaca ggacctgtgc agcgaggtct atcgctacca ggtgacgcca cgcatgctgt | 2340 |
| gtgccggcta ccgcaagggc aagaaggatg cctgtcaggg tgactcaggt ggtccgctgg | 2400 |

```
tgtgcaaggc actcagtggc cgctggttcc tggcggggct ggtcagctgg ggcctgggct    2460
gtggccggcc taactacttc ggcgtctaca cccgcatcac aggtgtgatc agctggatcc    2520
agcaagtggt gacctgagga actgccccc tgcaaagcag ggcccacctc ctggactcag     2580
agagcccagg gcaactgcca agcagggga caagtattct ggcgggggt gggggagaga     2640 gcaggccctg tggtggcagg aggtggcatc ttgtctcgtc cctgatgtct g             2691
```

<210> SEQ ID NO 5
<211> LENGTH: 1732
<212> TYPE: DNA
<213> ORGANISM: Homo sapiens

<400> SEQUENCE: 5

```
gttcttgagc cagacccagt ccagctctgg tgcctgccct ctggtgcgag ctgacctgag      60
atgcacttcc ctcctctgtg agctgtctcg gcacccactt gcagtcactg ccgcctgatg     120
ttgttactct tccactccaa aaggatgccc gtggccgagg ccccccaggt ggctggcggg     180 caggggacg gaggtgatgg cgaggaagcg gagccagagg ggatgttcaa ggcctgtgag      240
gactccaaga gaaaagcccg gggctacctc cgcctggtgc cctgtttgt gctgctggcc      300 ctgctcgtgc tggcttcggc ggggtgcta ctctggtatt cctagggta caaggcggag       360 gtgatggtca gccaggtgta ctcaggcagt ctgcgtgtac tcaatcgcca cttctcccag     420
gatcttaccc gccgggaatc tagtgccttc cgcagtgaaa ccgccaaagc ccagaagatg     480
ctcaaggagc tcatcaccag cacccgcctg gaacttact acaactccag ctccgtctat     540
tcctttgggg agggacccct cacctgcttc ttctggttca ttctccaaat ccccgagcac    600
cgccggctga tgctgagccc cgaggtggtg caggcactgc tggtggagga gctgctgtcc    660
acagtcaaca gctcggctgc cgtcccctac agggccgagt acgaagtgga ccccgagggc    720
ctagtgatcc tggaagccag tgtgaaagac atagctgcat tgaattccac gctgggttgt    780
taccgctaca gctacgtggg ccagggccag gtcctccggc tgaaggggcc tgaccacctg    840
gcctccagct gcctgtggca cctgcagggc cccaaggacc tcatgctcaa actccggctg    900
gagtggacgc tggcagagtg ccgggaccga ctggccatgt atgacgtggc cgggcccctg    960
gagaagaggc tcatcacctc ggtgtacggc tgcagccgcc aggagcccgt ggtggaggtt   1020
ctggcgtcgg gggccatcat ggcggtcgt tggaagaagg gcctgcacag ctactacgac    1080
cccttcgtgc tctccgtgca gccggtggtc ttccaggcct gtgaagtgaa cctgacgctg   1140
gacaacaggc tcgactccca gggcgtcctc agcaccccgt acttcccag ctactactcg    1200 ccccaaaccc actgctcctg gcacctcacg gtgccctctc tggactacgg cttggccctc   1260
tggtttgatg cctatgcact gaggaggcag aagtatgatt gccgtgcac ccagggccag    1320 tggacgatcc agaacaggag gtaccacttc ctctcctccc tctggcttcc tttcctccct    1380
ccccctccct ctcttccctc ctcaacagtg accccctcat tggaagccca agtccccaat   1440
ctcagagggg cagcaagggg agcgagcaga ggctggggct ggtgtcaggc ctgctgccct   1500
tgaccttgtc ctcgtcccaa cctccgcccct ggccccggct tccctctgg ctaccccaga   1560 ggtctcagac acgtttggtc atcagacacc ttgatgtttt attctaatta cagcaaaatt   1620
gtctcatctt cttgggtgct gtaaccccct ctggcaccct caatccttca ataaaatgtt    1680
tccagagcca aggaaaaaaa aaaaaaaaaa aaaaaaaaaa aaaaaaaaaa aa            1732
```

<210> SEQ ID NO 6

<211> LENGTH: 3143
<212> TYPE: DNA
<213> ORGANISM: Homo sapiens

<400> SEQUENCE: 6

| | | | | | |
|---|---|---|---|---|---|
| gagccaccta | ccctgctccg | aggccaggcc | tgcagggcct | catcggccag | agggtgatca | 60 |
| gtgagcagaa | ggatgcccgt | ggccgaggcc | ccccaggtgg | ctggcgggca | ggggacgga | 120 |
| ggtgatggcg | aggaagcgga | gccagagggg | atgttcaagg | cctgtgagga | ctccaagaga | 180 |
| aaagcccggg | gctacctccg | cctggtgccc | ctgtttgtgc | tgctggccct | gctcgtgctg | 240 |
| gcttcggcgg | gggtgctact | ctggtatttc | ctagggtaca | aggcggaggt | gatggtcagc | 300 |
| caggtgtact | caggcagtct | gcgtgtactc | aatcgccact | tctcccagga | tcttacccgc | 360 |
| cgggaatcta | gtgccttccg | cagtgaaacc | gccaaagccc | agaagatgct | caaggagctc | 420 |
| atcaccagca | cccgcctggg | aacttactac | aactccagct | ccgtctattc | ctttggggag | 480 |
| ggacccctca | cctgcttctt | ctggttcatt | ctccaaatcc | ccgagcaccg | ccggctgatg | 540 |
| ctgagccccg | aggtggtgca | ggcactgctg | gtggaggagc | tgctgtccac | agtcaacagc | 600 |
| tcggctgccg | tcccctacag | ggccgagtac | gaagtggacc | ccgagggcct | agtgatcctg | 660 |
| gaagccagtg | tgaaagacat | agctgcattg | aattccacgc | tgggttgtta | ccgctacagc | 720 |
| tacgtgggcc | agggccaggt | cctccggctg | aaggggcctg | accacctggc | ctccagctgc | 780 |
| ctgtggcacc | tgcagggccc | caaggacctc | atgctcaaac | tccggctgga | gtggacgctg | 840 |
| gcagagtgcc | gggaccgact | ggccatgtat | gacgtggccg | gcccctgga | agaggctc | 900 |
| atcacctcgg | tgtacggctg | cagccgccag | gagcccgtgg | tggaggttct | ggcgtcgggg | 960 |
| gccatcatgg | cggtcgtctg | gaagaagggc | ctgcacagct | actacgaccc | cttcgtgctc | 1020 |
| tccgtgcagc | cggtggtctt | ccaggcctgt | gaagtgaacc | tgacgctgga | caacaggctc | 1080 |
| gactcccagg | gcgtcctcag | cacccgtac | ttccccagct | actactcgcc | ccaaacccac | 1140 |
| tgctcctggc | acctcacggt | gccctctctg | gactacggct | tggccctctg | gtttgatgcc | 1200 |
| tatgcactga | ggaggcagaa | gtatgatttg | ccgtgcaccc | agggccagtg | gacgatccag | 1260 |
| aacaggaggc | tgtgtggctt | gcgcatcctg | cagcccacg | ccgagaggat | ccccgtggtg | 1320 |
| gccacggccg | ggatcaccat | caacttcacc | tcccagatct | ccctcaccgg | gcccggtgtg | 1380 |
| cgggtgcact | atggcttgta | caaccagtcg | gaccccctgcc | ctggagagtt | cctctgttct | 1440 |
| gtgaatggac | tctgtgtccc | tgcctgtgat | ggggtcaagg | actgccccaa | cggcctggat | 1500 |
| gagagaaact | gcgtttgcag | agccacattc | cagtgcaaag | aggacagcac | atgcatctca | 1560 |
| ctgcccaagg | tctgtgatgg | gcagcctgat | tgtctcaacg | gcagcgatga | agagcagtgc | 1620 |
| caggaagggg | tgccatgtgg | gacattcacc | ttccagtgtg | aggaccggag | ctgcgtgaag | 1680 |
| aagcccaacc | cgcagtgtga | tgggcggccc | gactgcaggg | acggctcgga | tgaggagcac | 1740 |
| tgtgactgtg | gcctccaggg | cccctccagc | cgcattgttg | gtgagctgt | gtcctccgag | 1800 |
| ggtgagtggc | catggcaggc | cagcctccag | gttcggggtc | gacacatctg | tgggggggcc | 1860 |
| ctcatcgctg | accgctgggt | gataacagct | gcccactgct | tccaggagga | cagcatggcc | 1920 |
| tccacggtgc | tgtggaccgt | gttcctgggc | aaggtgtggc | agaactcgcg | ctggcctgga | 1980 |
| gaggtgtcct | tcaaggtgag | ccgcctgctc | ctgcacccgt | accacgaaga | ggacagccat | 2040 |
| gactacgacg | tggcgctgct | gcagctcgac | cacccggtgg | tgcgctcggc | cgccgtgcgc | 2100 |
| cccgtctgcc | tgccgcgcg | ctcccacttc | ttcgagcccg | gctgcactg | ctggattacg | 2160 |
| ggctggggcg | ccttgcgcga | gggcggcccc | atcagcaacg | ctctgcagaa | agtggatgtg | 2220 |

```
cagttgatcc cacaggacct gtgcagcgag gcctatcgct accaggtgac gccacgcatg    2280
ctgtgtgccg gctaccgcaa gggcaagaag gatgcctgtc agggtgactc aggtggtccg    2340
ctggtgtgca aggcactcag tggccgctgg ttcctggcgg ggctggtcag ctggggcctg    2400
ggctgtggcc ggcctaacta cttcggcgtc tacacccgca tcacaggtgt gatcagctgg    2460
atccagcaag tggtgacctg aggaactgcc ccctgcaaa gcagggccca cctcctggac     2520
tcagagagcc cagggcaact gccaagcagg ggacaagta ttctggcggg gggtggggga     2580
gagagcaggc cctgtggtgg caggaggtgg catcttgtct cgtccctgat gtctgctcca    2640
gtgatggcag gaggatggag aagtgccagc agctgggggt caagacgtcc cctgaggacc    2700
caggcccaca cccagcccTT ctgcctccca attctctctc ctccgtcccc ttcctccact    2760
gctgcctaat gcaaggcagt ggctcagcag caagaatgct ggttctacat cccgaggagt    2820
gtctgaggtg cgccccactc tgtacagagg ctgtttgggc agccttgcct ccagagagca    2880
gattccagct tcggaagccc ctggtctaac ttgggatctg ggaatggaag gtgctcccat    2940
cggaggggac cctcagagcc tggagactg ccaggtgggc ctgctgccac tgtaagccaa     3000
aaggtgggga agtcctgact ccagggtcct tgccccaccc ctgcctgcca cctgggccct    3060
cacagcccag accctcactg ggaggtgagc tcagctgccc tttggaataa agctgcctga    3120
tcaaaaaaaa aaaaaaaaaa aaa                                           3143

<210> SEQ ID NO 7
<211> LENGTH: 528
<212> TYPE: DNA
<213> ORGANISM: Homo sapiens
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t

<400> SEQUENCE: 7
aaaaaggcag ggaagtcctg cttccgtgcc ccaccggtgc tcagcagagg ctcccttgca     60
aatgcgaggc tgtttccaac tttggtctgt ttccctggca ggatgcccgt ggccgaggcc    120
ccccaggtgg ctggcgggca gggggacgga ggtgatggcg aggaagcngg agccggaggg    180
gatgttcaag gcctgtgagg actccaagag aaaagcccgg ggctacctcc gcctggtgcc    240
cctgtttgtg ctgctggccc tgctcgtgct ggcttcggcg ggggtgctac tctggtattt    300
cctagggtac aaggcggagg tgatggtcag ccaggtgtac tcaggcagtc tgcgtgtact    360
caatcgccac ttctcccagg atcttacccg ccgggaatct agtgccttcc gcagtgaaac    420
cgccaaagcc canaagatgc tcaaggagct catcaccagc acccgcctgg gaacttacta    480
caactccagc tccgtctatt cctttgggga gggacccctc acctgctt                528

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
aggccttccg ggtccacctc                                                20
```

```
<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
tttctttcct acagagaccc                                               20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
agccttgata gaggcacctt                                               20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
gcttagagta cagcccactt                                               20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
tcaccaggcc ttccgggtcc                                               20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
aggcatccta accaccagct                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
ccttccctga aggttcctcc                                               20

<210> SEQ ID NO 15
<211> LENGTH: 20
<212> TYPE: DNA
<213> ORGANISM: Artificial sequence
<220> FEATURE:
<223> OTHER INFORMATION: Primer
```

```
<400> SEQUENCE: 15
attccacgct gggctgttat                                                      20

<210> SEQ ID NO 16
<211> LENGTH: 18
<212> TYPE: DNA
<213> ORGANISM: Artificial sequence
<220> FEATURE:
<223> OTHER INFORMATION: Primer

<400> SEQUENCE: 16
ctggtcaggc cccttcaa                                                        18

<210> SEQ ID NO 17
<211> LENGTH: 22
<212> TYPE: DNA
<213> ORGANISM: Artificial sequence
<220> FEATURE:
<223> OTHER INFORMATION: Probe

<400> SEQUENCE: 17
tgaacccagg ccaggtcctc cc                                                   22

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
tgcagaagag aaggaagaga gaca                                                 24

<210> SEQ ID NO 19
<211> LENGTH: 24
<212> TYPE: DNA
<213> ORGANISM: Artificial sequence
<220> FEATURE:
<223> OTHER INFORMATION: Primer

<400> SEQUENCE: 19
cacactggga attgttacag catt                                                 24

<210> SEQ ID NO 20
<211> LENGTH: 28
<212> TYPE: DNA
<213> ORGANISM: Artificial sequence
<220> FEATURE:
<223> OTHER INFORMATION: Probe

<400> SEQUENCE: 20
caacttcccc atctgcatct tctgctgt                                             28
```

MODULATION OF TMPRSS6 EXPRESSION

SEQUENCE LISTING

The present application is being filed along with a Sequence Listing in electronic format. The Sequence Listing is provided as a file entitled BIOL0162USC2SEQ.txt created Dec. 19, 2017, which is 72 kb in size. The information in the electronic format of the sequence listing is incorporated herein by reference in its entirety.

FIELD OF THE INVENTION

The present invention provides methods, compounds, and compositions for modulating TMPRSS6 expression for the purpose of reducing iron accumulation in an animal.

BACKGROUND OF THE INVENTION

Maintenance of iron balance in human beings is delicate because of the limited capacity of the human physiology for iron absorption and excretion (Finch, C. A. and Huebers, H. N. Engl. J. Med. 1982. 306: 1520-1528). Iron deficiency is a widespread disorder and results from any condition in which dietary iron intake does not meet the body's demands. Often, pathological blood loss contributes to negative iron balance. Iron overload is also a common condition, and may result from a genetic cause, for example, mutations of different genes of iron metabolism (Camaschella, C. Blood. 2005. 106: 3710-3717). The hepatic peptide hormone, hepcidin plays a key role in body iron metabolism as it controls iron absorption and recycling (Ganz, T. Am. Soc. Hematol. Educ. Program 2006. 507: 29-35; Kemna, E. H. et al., Clin. Chem. 2007. 53: 620-628). Several proteins, including HFE (hemochromatosis protein) (Ahmad, K. A. et al., Blood Cells Mol Dis. 2002. 29: 361), transferrin receptor 2 (Kawabata, H. et al., Blood 2005. 105: 376), and hemojuvelin (Papanikolaou, G. et al., Nat. Genet. 2004. 36: 77) also regulate the body's iron levels.

Transmembrane protease, serine 6 (TMPRSS6) is a type II transmembrane serine protease and is expressed primarily in the liver (Velasco, G. et al., J. Biol. Chem. 2002. 277: 37637-37646). Mutations in TMPRSS6 have been implicated in iron deficiency anemia (Finberg, K. E. et al., Nat. Genet. 2008. 40: 569-571), where the level of hepcidin was found to be unusually elevated. A study of a human population with microcytic anemia found that loss-of-function mutations in the TMPRSS6 gene lead to overproduction of hepcidin, which, in turn, lead to defective iron absorption and utilization (Melis, M. A. et al., Hematologica 2008. 93: 1473-1479). TMPRSS6 participates in a transmembrane signaling pathway triggered by iron deficiency and suppresses diverse pathways of Hamp activation, the gene that encodes hepcidin (Du, X. et al., Science 2008. 320: 1088-1092). Heterozygous loss of TMPRSS6 in HFE$^{-/-}$ mice reduces systemic iron overload, while homozygous loss of TMPRSS6 in HFE$^{-/-}$ mice causes systemic iron deficiency and elevated hepatic expression of hepcidin (Finberg, K. E. et al., Blood 2011. 117: 4590-4599).

An example of an iron overload disorder is Hemochromatosis. Hemochromatosis (e.g. hemochromatosis type 1 or hereditary hemochromatosis) is a disorder that results in excess intestinal absorption of dietary iron from the gastrointestinal tract (Allen, K. J. et al., N. Engl. J. Med. 2008. 358: 221-230). This results in a pathological increase in total body iron stores. Excess iron accumulates in tissues and organs, particularly the liver, adrenal glands, heart, skin, gonads, joints and pancreas, and disrupt their normal function. Secondary complications, such as cirrhosis (Ramm, G. A. and Ruddell, R. G. Semin. Liver Dis. 2010. 30: 271-287), polyarthropathy (Carroll, G. J. et al., Arthritis Rheum. 2011. 63: 286-294), adrenal insufficiency, heart failure and diabetes (Huang, J. et al., Diabetes 2011. 60: 80-87) are common. Another example of an iron overload disorder is β-thalassemia, where patients can develop iron overload caused by ineffective erythropoiesis or transfusions to treat β-thalassemia.

There is a currently a lack of acceptable options for treating iron overload disorders. It is therefore an object herein to provide compounds and methods for the treatment of such diseases and disorders. This invention relates to the discovery of novel, highly potent inhibitors of TMPRSS6 gene expression.

All documents, or portions of documents, cited in this application, including, but not limited to, patents, patent applications, articles, books, and treatises, are hereby expressly incorporated-by-reference for the portions of the document discussed herein, as well as in their entirety.

SUMMARY OF THE INVENTION

Provided herein are methods for modulating the levels of TMPRSS6 mRNA and/or protein in an animal. Provided herein are methods, compounds, and compositions for lowering TMPRSS6 levels. In certain embodiments, lowering of TMPRSS6 results in an increase in hepcidin expression levels. In certain embodiments, lowering of TMPRSS6 results in a decrease in the percentage of saturation of transferrin. In certain embodiments, lowering of TMPRSS6 results in a reduction of iron accumulation. In certain embodiments, such results are effected by administering a TMPRSS6 inhibitor. In certain embodiments, a therapeutically effective amount of a TMPRSS6 inhibitor is administered to an animal. In further embodiments, administration of the therapeutically effective amount of the TMPRSS6 inhibitor also increases hepcidin expression levels. In further embodiments, administration of the therapeutically effective amount of the TMPRSS6 inhibitor also decreases the percentage of saturation of the transferrin molecule in the animal.

In certain embodiments, methods are provided for treating, preventing, delaying the onset of, ameliorating and/or reducing a symptom, of a disease, disorder and/or condition associated with the excess accumulation of iron in an animal. The methods comprise of administering to the animal a therapeutically effective amount of a TMPRSS6 inhibitor, wherein the disease, disorder and/or condition associated with excess iron accumulation is treated, prevented, the onset delayed, the symptom ameliorated and/or reduced.

In certain embodiments, methods are provided for identifying an animal at risk for a disease, disorder and/or condition or having a disease, disorder and/or condition which is associated with excess accumulation of iron. In further embodiments, methods include administering to the animal a therapeutically effective amount of a TMPRSS6 inhibitor, thus treating the animal.

In certain embodiments, provided herein is the use of a TMPRSS6 inhibitor for the preparation of a medicament.

In certain embodiments, provided herein is the use of a TMPRSS6 inhibitor as a medicament for treating, preventing, delaying the onset of, and/or reducing the symptom of a disease, disorder and/or condition associated with excess accumulation of iron in an animal by administering to the animal a therapeutically effective amount of the TMPRSS6 inhibitor.

In certain embodiments, provided herein is the use of a TMPRSS6 antisense compound as an inhibitor of TMPRSS6.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" or "Pharmaceutical agent" means the substance or substances in a pharmaceutical composition that provide a therapeutic benefit when administered to an individual. For example, in certain embodiments, an antisense oligonucleotide targeted to TMPRSS6 is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Agent" means an active substance that can provide a therapeutic benefit when administered to an animal. "First Agent" means a therapeutic compound provided herein. For example, a first agent is an antisense oligonucleotide targeting TMPRSS6. "Second agent" means a second therapeutic compound described herein. For example, a second agent can be a second antisense oligonucleotide targeting TMPRSS6 or a non-TMPRSS6 target. Alternatively, a second agent can be a compound other than an antisense oligonucleotide.

"Amelioration" refers to a lessening of at least one indicator, marker, sign, or symptom of an associated disease, disorder and/or condition. In certain embodiments, amelioration includes a delay or slowing in the progression of one or more indicators of a condition, disorder and/or disease. The severity of indicators may be determined by subjective or objective measures, which are known to those skilled in the art.

"Anemia" is a disease characterized by a lower than normal number of red blood cells (erythrocytes) in the blood, usually measured by a decrease in the amount of hemoglobin. The cause of anemia can include chronic inflammation, chronic kidney disease, kidney dialysis treatment, genetic disorders, chronic infection, acute infection, cancer and cancer treatments. Altered iron homeostasis and/or erythropoiesis in these diseases, disorders and/or conditions can also result in decreased erythrocyte production. Clinical signs of anemia include low serum iron (hypoferremia), low hemoglobin levels, low hematocrit levels, decreased red blood cells, decreased reticulocytes, increased soluble transferrin receptor and iron restricted erythropoiesis. Examples of anemia include thalassemias (i.e. α-thalassemia, β-thalassemia (minor, intermedia and major) and δ-thalassemia), sickle cell anemia, aplastic anemia, Fanconi anemia, Diamond Blackfan anemia, Shwachman Diamond syndrome, red cell membrane disorders, glucose-6-phosphate dehydrogenase deficiency, hereditary hemorrhagic telangiectasia, hemolytic anemia, anemia of chronic disease and the like.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Blood transfusion" refers to the process of receiving blood products into one's circulation intravenously. Transfusions are used in a variety of medical disease, disorder and/or conditions to replace lost blood components.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses concomitant, parallel or sequential administration.

"Complementarity" means the capacity for pairing between nucleobases of a first nucleic acid and a second nucleic acid.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diluent" means an ingredient in a composition that lacks pharmacological activity, but is pharmaceutically necessary or desirable. For example, the diluent in an injected composition may be a liquid, e.g. PBS.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means that each nucleobase of a nucleobase sequence of a first nucleic acid has a complementary nucleobase in a second nucleobase sequence of a second nucleic acid. In certain embodiments, the first nucleic acid is an antisense compound and the second nucleic acid is a target nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxynucleosides positioned between and immediately adjacent to 5' and 3' wing segments having from one to six nucleosides.

"Hemochromatosis" is a disorder of iron metabolism that results in excess iron being absorbed from the gastrointestinal tract, leading to excess iron accumulation and deposition in various tissues of the body. Primary or hereditary or classic hemochromatosis is caused by a genetic mutation, for example, in the HFE gene. Subjects with this disease have excess amounts of iron, which is absorbed in the gastrointestinal tract and builds up in the body tissues, particularly in the liver. Secondary or acquired hemochromatosis can be caused by frequent blood transfusions, high oral or parenteral intake of iron supplements, or a secondary effect of other diseases.

"Hematopoiesis" refers to the formation of cellular components of the blood, derived from hematopoietic stem cells. These stem cells reside in the medulla of the bone marrow and have the unique ability to give rise to all the different mature blood cell types.

"Hemolysis" refers to the rupturing of erythrocytes or red blood cells and the release of their contents into surrounding fluid. Hemolysis in an animal may occur due to a large number of medical conditions, including bacterial infection, parasitic infection, autoimmune disorders and genetic disorders.

"Hepcidin" refers to both an mRNA as well as a protein encoded by the mRNA that is produced by hepatocytes in response to inflammation or to rising levels of iron in the blood. The primary role of hepcidin is to regulate blood iron levels by facilitating a decrease in these blood iron levels. Hepcidin expression is increased in conditions of acute and chronic inflammation resulting in decreased iron availability for erythropoiesis. "Hepcidin" is also referred to as hepcidin antimicrobial peptide; HAMP; HAMP1; HEPC; HFE2; LEAP-1; LEAP1; and liver-expressed antimicrobial peptide.

"Hereditary anemia" refers to anemia which is caused by a hereditary condition that causes red blood cells in the body to die faster than normal, be ineffective in transporting oxygen from the lungs to the different parts of the body, or not be created at all. Examples include, but are not limited to, sickle cell anemia, thalassemia, Fanconi anemia, Diamond Blackfan anemia, Shwachman Diamond syndrome, red cell membrane disorders, glucose-6-phosphate dehydrogenase deficiency, or hereditary hemorrhagic telangiectasia.

"HFE" refers to the human hemochromatosis gene or protein.

"HFE gene mutation" refers to mutations in the HFE gene, which may result in hereditary hemochromatosis.

"Hybridization" means the annealing of complementary nucleic acid molecules. In certain embodiments, complementary nucleic acid molecules include an antisense compound and a target nucleic acid.

"Identifying an animal at risk for or having a disease, disorder and/or condition associated with excess accumulation of iron" means identifying an animal having been diagnosed with a disease, disorder and/or condition or identifying an animal predisposed to develop a disease, disorder and/or condition associated with excess accumulation of iron. Individuals can be predisposed to develop a disease, disorder and/or condition associated with excess accumulation of iron in individuals with a familial history of hemochromatosis. Such identification may be accomplished by any method including evaluating an individual's medical history and standard clinical tests or assessments.

"Immediately adjacent" means that there are no intervening elements between the immediately adjacent elements.

"Individual" or "subject" or "animal" means a human or non-human animal selected for treatment or therapy.

"Inhibiting the expression or activity" refers to a reduction or blockade of the expression or activity of a RNA or protein and does not necessarily indicate a total elimination of expression or activity.

"Internucleoside linkage" refers to the chemical bond between nucleosides.

"Intravenous administration" means administration into a vein.

"Iron accumulation" or "iron overload" indicates accumulation and deposition of iron in the body from any cause. The most common causes are hereditary causes, transfusional iron overload, which can result from repeated blood transfusions, or excessive dietary iron intake.

"Iron supplements" refer to supplements prescribed for a medical reason to treat iron deficiency in a patient. Iron can be supplemented by the oral route or given parenterally.

"Linked nucleosides" means adjacent nucleosides which are bonded together.

"Marker" or "biomarker" is any measurable and quantifiable biological parameter that serves as an index for health- or physiology-related assessments. For example, an increase in the percentage saturation of transferrin, an increase in iron levels, or a decrease in hepcidin levels can be considered markers of an iron overload disease, disorder and/or condition.

"MCH" refers to "mean corpuscular hemoglobin" or "mean cell hemoglobin", a value to express the average mass of hemoglobin (Hb) per red blood cell in a sample of blood.

"MCV" referes to "mean corpuscular volume" or "mean cell volume", a value to express the average red blood cell size.

"Mismatch" or "non-complementary nucleobase" or "MM" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. For example, a modified nucleobase can be 5'-methylcytosine. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety or modified nucleobase.

"Modified nucleotide" means a nucleotide having, independently, a modified sugar moiety, modified internucleoside linkage, or modified nucleobase.

"Modified oligonucleotide" means an oligonucleotide comprising a modified internucleoside linkage, a modified sugar, or a modified nucleobase.

"Modified sugar" refers to a substitution or change from a natural sugar. For example, a modified sugar can be 2'-MOE.

"Modulating" refers to changing or adjusting a feature in a cell, tissue, organ or organism. For example, modulating TMPRSS6 level can mean to increase or decrease the level of TMPRSS6 mRNA or TMPRSS6 protein in a cell, tissue, organ or organism. A "modulator" effects the change in the cell, tissue, organ or organism. For example, a TMPRSS6 antisense oligonucleotide can be a modulator that increases or decreases the amount of TMPRSS6 mRNA or TMPRSS6 protein in a cell, tissue, organ or organism.

"Motif" means the pattern of chemically distinct regions in an antisense compound.

"Mutations" refer to changes in a nucleic acid sequence. Mutations can be caused in a variety of ways including, but not limited to, radiation, viruses, transposons and mutagenic chemicals, as well as errors that occur during meiosis, DNA replication, RNA transcription and post-transcriptional processing. Mutations can result in several different changes in sequence; they can have either no effect, alter the product of a gene, or prevent the gene from functioning properly or completely. For example, HFE mutation can lead to the improper functioning of the gene product, leading to excess iron absorption in the intestines.

"Myelodysplastic syndrome" refers to a diverse collection of hematological medical disease, disorder and/or conditions that involve ineffective production of the myeloid class of blood cells. The syndrome is caused by disorders of the stem cells in the bone marrow. In myelodysplastic syndrome, hematopoiesis is ineffective and the number and quality of blood cells declines irreversibly, further impairing blood production. As a result, patients with myelodysplastic syndrome develop severe anemia and require frequent blood transfusions.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound; such as, for example, nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound; such as, for example, peptide nucleic acids or morpholinos (morpholinos linked by —N(H)—C(=O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intra-arterial administration, intraperitoneal administration, or intracranial administration, e.g. intrathecal or intracerebroventricular administration. Administration can be continuous, or chronic, or short or intermittent.

"Peptide" refers to a molecule formed by linking at least two amino acids by amide bonds. Peptide refers to polypeptides and proteins.

"Percentage saturation of transferrin" refers to the ratio of serum iron to total iron binding capacity multiplied by 100. Of the transferrin molecules that are available to bind iron, this value tells a clinician how much serum iron are actually bound.

"Pharmaceutical composition" means a mixture of substances suitable for administering to an individual. For example, a pharmaceutical composition may comprise one or more active pharmaceutical agents and a sterile aqueous solution.

"Pharmaceutically acceptable carrier" means a medium or diluent that does not interfere with the structure of the oligonucleotide. Certain of such carriers enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution, such as PBS.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Polycythemia" refers to a condition of increased red blood cells (RBCs) in a specified volume due to either an increase in red blood cell numbers (absolute polycythemia) or a decrease in plasma volume (relative polycythemia). Blood volume to red blood cell proportions can be measured as Hematocrit levels. The increased proportion of RBCs can make the blood viscous which can lead to slower blood flow through the circulatory system and potential formation of blood clots. Slower blood flow can decrease oxygen transport to cells, tissue and/or organs leading to diseases, disorders or conditions such as angina or heart failure. Formation of blood clots in the circulatory system can lead to cell, tissue and/or organ damage leading to diseases, disorders or conditions such as myocardial infarction or stroke. Treatment for polycythemia includes phlebotomy or drugs to decrease RBC production (e.g., INF-α, hydroxyurea, anagrelide). Examples of polycythemia include, but is not limited to, polycythemia vera (PCV), polycythemia rubra vera (PRV) and erythremia. In certain instances, polycythemia can progress into erythroid leukemia in a subject.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset, development, or progression of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity with a target nucleic acid to induce a desired effect, while exhibiting minimal or no effects on non-target nucleic acids under conditions in which specific binding is desired, i.e. under physiological conditions in the case of in vivo assays and therapeutic treatments.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Thalassemia" refers to a subgroup of anemias (e.g., α-thalassemia, β-thalassemia, δ-thalassemia, non-transfusion dependent thalassemia (NTDT)) caused by the formation of abnormal hemoglobin molecules leading to the destruction or degradation of red blood cells. Complications of thalassemia include excess iron (i.e. iron overload in the blood either from the thalassemia itself or from frequent transfusions to treat the thalassemia), increased risk of infection, bone deformities, enlarged spleens (i.e. splenomegaly), slowed growth rates and heart problems (e.g., congestive heart failure and arrhythmias).

"Therapeutically effective amount" means an amount of a pharmaceutical agent that provides a therapeutic benefit to an individual.

"TMPRSS6" (also known as "matriptase-2") refers to any nucleic acid or protein of TMPRSS6.

"TMPRSS6 nucleic acid" means any nucleic acid encoding TMPRSS6. For example, in certain embodiments, a TMPRSS6 nucleic acid includes a DNA sequence encoding TMPRSS6, an RNA sequence transcribed from DNA encoding TMPRSS6 (including genomic DNA comprising introns and exons), and a mRNA sequence encoding TMPRSS6. "TMPRSS6 mRNA" means a mRNA encoding a TMPRSS6 protein.

"TMPRSS6 specific inhibitor" refers to any agent capable of specifically inhibiting the expression of TMPRSS6 gene, TMPRSS6 RNA and/or TMPRSS6 protein at the molecular level. For example, TMPRSS6 specific inhibitors include nucleic acids (including antisense compounds), peptides, antibodies, small molecules, and other agents capable of inhibiting the level of TMPRSS6. In certain embodiments, by specifically modulating TMPRSS6, TMPRSS6 specific inhibitors may affect components of the iron accumulation pathway.

"Treat" refers to administering a pharmaceutical composition to an animal in order to effect an alteration or improvement of a disease, disorder, or condition in the animal. In certain embodiments, one or more pharmaceutical compositions can be administered to the animal.

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleotide) or a DNA nucleotide (i.e. β-D-deoxyribonucleotide).

Certain Embodiments

In certain embodiments, provided herein are TMPRSS6 modulators. In certain embodiments, the TMPRSS6 modulators can be TMPRSS6 specific inhibitors. In certain embodiments, TMPRSS6 specific inhibitors are nucleic acids (including antisense compounds), peptides, antibodies, small molecules, and other agents capable of inhibiting or lowering the expression of TMPRSS6.

In certain embodiments, methods are provided herein for reducing iron accumulation. In certain embodiments, provided are TMPRSS6 inhibitors as described herein for use in reducing iron accumulation in an animal. In certain embodiments, the iron accumulation is the result of a therapy to treat a disease, disorder or condition in the animal. In certain embodiments, the therapy is transfusion therapy. In certain embodiments, the iron accumulation is due to a disease, disorder or condition in the animal. In certain embodiments, the disease, disorder or condition is hereditary hemochromatosis or β-thalassemia. In certain embodiments, the β-thalassemia is β-thalassemia major, β-thalassemia intermedia or β-thalassemia minor.

In certain embodiments, methods are provided herein for increasing hepcidin levels, such as mRNA or protein expression levels. In certain embodiments, provided are TMPRSS6 inhibitors as described herein for use in increasing hepcidin levels, such as mRNA expression levels.

In certain embodiments, methods are provided herein for decreasing the percentage saturation of transferrin in an animal. In certain embodiments, provided are TMPRSS6 inhibitors as described herein for use in decreasing the percentage saturation of transferrin in an animal. In certain embodiments, decreasing transferrin saturation leads to a decrease in iron supply for erythropoiesis. In certain embodiments, the decrease in erythropoiesis treats, prevents, delays the onset of, ameliorates, and/or reduces polycythemia, or symptom thereof, in the animal. In certain embodiments, the polycythemia is polycythemia vera. In certain embodiments, treatment with the modified oligonucleotide targeting TMPRSS6 prevents or delays the polycythemia from progressing into erythroid leukemia.

Methods provided herein comprise administering to the animal a therapeutically effective amount of the TMPRSS6 inhibitor. In certain embodiments, provided are TMPRSS6 inhibitors as described herein for use in administration to an animal in a therapeutically effective amount.

In certain embodiments, methods are provided for treating, preventing, delaying the onset of, ameliorating and/or reducing a disease, disorder and/or condition, or symptom thereof, associated with the excess accumulation of iron in an animal, comprising administering to the animal a therapeutically effective amount of a TMPRSS6 inhibitor, wherein the disease, disorder and/or condition associated with excess iron accumulation is treated, prevented, the onset delayed, the symptom ameliorated or reduced.

In certain embodiments, methods are provided for treating, preventing, delaying the onset of, ameliorating, and/or reducing hereditary hemochromatosis, or symptom thereof, in an animal, comprising administering to the animal a therapeutically effective amount of a modified oligonucleotide targeting TMPRSS6, wherein the modified oligonucleotide comprises (a) a gap segment consisting of linked deoxy nucleosides (b) a 5' wing segment consisting of linked nucleosides (c) a 3' wing segment consisting of linked nucleosides, and wherein the gap segment is positioned between the 5' wing segment and the 3' wing segment and wherein each nucleoside of each wing segment comprises a modified sugar.

In certain embodiments, methods are provided for treating, preventing, delaying the onset of, ameliorating, and/or reducing anemia, or symptom thereof, in an animal, comprising administering to the animal a therapeutically effective amount of a modified oligonucleotide targeting TMPRSS6, wherein the modified oligonucleotide comprises (a) a gap segment consisting of linked deoxy nucleosides (b) a 5' wing segment consisting of linked nucleosides (c) a 3' wing segment consisting of linked nucleosides, and wherein the gap segment is positioned between the 5' wing segment and the 3' wing segment and wherein each nucleoside of each wing segment comprises a modified sugar.

In certain embodiments, methods are provided for treating, preventing, delaying the onset of, ameliorating, and/or reducing β-thalassemia, or symptom thereof, in an animal, comprising administering to the animal a therapeutically effective amount of a modified oligonucleotide targeting TMPRSS6, wherein the modified oligonucleotide comprises (a) a gap segment consisting of linked deoxy nucleosides (b) a 5' wing segment consisting of linked nucleosides (c) a 3' wing segment consisting of linked nucleosides, and wherein the gap segment is positioned between the 5' wing segment and the 3' wing segment and wherein each nucleoside of each wing segment comprises a modified sugar.

In certain embodiments, methods are provided for decreasing transferrin saturation in an animal, comprising administering to the animal a therapeutically effective amount of a modified oligonucleotide targeting TMPRSS6, wherein the modified oligonucleotide comprises (a) a gap segment consisting of linked deoxy nucleosides (b) a 5' wing segment consisting of linked nucleosides (c) a 3' wing segment consisting of linked nucleosides, and wherein the gap segment is positioned between the 5' wing segment and the 3' wing segment and wherein each nucleoside of each wing segment comprises a modified sugar. In certain embodiments, decreasing transferrin saturation leads to a decrease in iron supply for erythropoiesis. In certain embodiments, the decrease in erythropoiesis treats, prevents, delays the onset of, ameliorates, and/or reduces polycythemia, or symptom thereof, in the animal. In certain embodiments, the polycythemia is polycythemia vera. In certain embodiments, treatment with the modified oligonucleotide targeting TMPRSS6 prevents or delays the polycythemia from progressing into erythroid leukemia.

In certain embodiments, methods are provided for identifying an animal at risk for a disease, disorder and/or condition or having a disease, disorder and/or condition which is associated with excess accumulation of iron, administering to the animal a therapeutically effective amount of a TMPRSS6 inhibitor, thereby treating the animal.

In certain embodiments, provided herein is the use of a TMPRSS6 inhibitor for the preparation of a medicament. In certain embodiments, are provided TMPRSS6 inhibitors as described herein for use in the preparation of a medicament.

In certain embodiments, provided herein is the use of a TMPRSS6 inhibitor as a medicament for treating, preventing, delaying the onset of, and/or reducing a disease, disorder and/or condition, or symptom thereof, associated with excess accumulation of iron in an animal by administering to the animal a therapeutically effective amount of the TMPRSS6 inhibitor. In certain embodiments are provided TMPRSS6 inhibitors as described herein for use in treating, preventing, delaying the onset of, and/or reducing a disease, disorder and/or condition, or symptom thereof, associated with excess accumulation of iron in an animal.

In certain embodiments, provided herein is the use of a TMPRSS6 antisense compound for inhibiting TMPRSS6. In certain embodiments, provided herein is a TMPRSS6 antisense compound for use in inhibiting TMPRSS6.

In certain embodiments, the disease is hemochromatosis. In certain embodiments, the disease is associated with mutations in the HFE gene. In other embodiments, the disease is associated with mutations in the hemojuvelin gene. In other embodiments, the disease is associated with mutations in the hepcidin gene.

In certain embodiments, provided herein is the use of a TMPRSS6 inhibitor as a medicament for treating, preventing, delaying the onset of, and/or reducing polycythemia or erythoid leukemia. In certain embodiments are provided TMPRSS6 inhibitors as described herein for use in treating, preventing, delaying the onset of, and/or reducing polycythemia or erythoid leukemia. In certain embodiments, the polycythemia includes, but is not limited to, polycythemia vera (PCV), polycythemia rubra vera (PRV) and erythremia In certain embodiments, the disease, disorder and/or condition may be due to multiple blood transfusions. In certain embodiments, multiple transfusions may lead to polycythemia. In further embodiments, multiple blood transfusions are associated with the animal having anemia. Examples of anemia requiring multiple blood transfusions are hereditary anemia, myelodysplastic syndrome and severe chronic hemolysis. Examples of hereditary anemia include, but are not limited to, sickle cell anemia, thalassemia, Fanconi anemia, Diamond Blackfan anemia, Shwachman Diamond syndrome, red cell membrane disorders, glucose-6-phosphate dehydrogenase deficiency, or hereditary hemorrhagic telangiectasia. In certain embodiments, the thalassemia is β-thalassemia. In certain embodiments, the β-thalassemia is β-thalassemia major, β-thalassemia intermedia or β-thalassemia minor. In certain embodiments, the disease, disorder and/or condition is associated with excess parenteral iron supplement intake or excess dietary iron intake.

In certain embodiments, provided herein are compounds targeted to a TMPRSS6 nucleic acid. In certain embodiments, the TMPRSS6 nucleic acid is the murine sequence set forth in GENBANK Accession No. NM_027902.2 (incorporated herein as SEQ ID NO: 1). In certain embodiments, the TMPRSS6 nucleic acid is any of the human sequences set forth in GENBANK Accession No. NM_153609.2 (incorporated herein as SEQ ID NO: 2), the complement of GENBANK Accession No. NT_011520.12 truncated from 16850000 to 16891250 (incorporated herein as SEQ ID NO: 3), GENBANK Accession No. CR456446.1 (incorporated herein as SEQ ID NO: 4), GENBANK Accession No. BC039082.1 (incorporated herein as SEQ ID NO: 5), GENBANK Accession No. AY358398.1 (incorporated herein as SEQ ID NO: 6), or GENBANK Accession No. DB081153.1 (incorporated herein as SEQ ID NO: 7).

In certain embodiments, the TMPRSS6 nucleic acid is a modified oligonucleotide. In certain embodiments, TMPRSS6 nucleic acid consists of 12 to 30, 10 to 30, 8 to 80, 10 to 50, 15 to 30, 18 to 21, 20 to 80, 20 to 35, 20 to 30, 20 to 29, 20 to 28, 20 to 27, 20 to 26, 20 to 25, 20 to 24, 20 to 23, 20 to 22, 20 to 21 or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In further embodiments, the modified oligonucleotide is single-stranded.

In certain embodiments, the compound for use in the methods can comprise a modified oligonucleotide comprising a nucleobase sequence at least 70%, at least 75%, at least 80%, at least 85%, 90%, at least 95%, at least 96%, at least 97%, at least 98%, or at least 99% complementary to an equal length portion of SEQ ID NOs: 1-7. In certain embodiments, the compound can comprise a modified oligonucleotide comprising a nucleobase sequence 100% complementary to an equal length portion of SEQ ID NOs: 1-7.

In certain embodiments, provided are compounds for use in the methods comprising a modified oligonucleotide having a nucleobase sequence comprising at least 8, at least 9, at least 10, at least 11, at least 12, at least 13, at least 14, at least 15, at least 16, at least 17, at least 18, at least 19 or at least 20 contiguous nucleobases of a nucleobase sequence complementary to any of the sequences recited in SEQ ID NOs: 1-7.

In certain embodiments, the modified oligonucleotide for use in the methods consists of TMPRSS6 nucleic acid consists of 12 to 30, 10 to 30, 8 to 80, 10 to 50, 15 to 30, 18 to 21, 20 to 80, 20 to 35, 20 to 30, 20 to 29, 20 to 28, 20 to 27, 20 to 26, 20 to 25, 20 to 24, 20 to 23, 20 to 22, 20 to 21 or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the compound for use in the methods has at least one modified internucleoside linkage. In certain embodiments, the modified internucleoside linkage is a phosphorothioate internucleoside linkage In certain embodiments, the compound for use in the methods has at least one nucleoside comprising a modified sugar. In certain embodiments, at least one modified sugar is a bicyclic sugar.

In certain embodiments, the compound for use in the methods has at least one nucleoside comprising a modified nucleobase. In certain embodiments, the modified nucleobase is a 5-methylcytosine.

In certain embodiments, the modified oligonucleotide of the compound for use in the methods comprises: (i) a gap segment consisting of linked deoxynucleosides; (ii) a 5' wing segment consisting of linked nucleosides; (iii) a 3' wing segment consisting of linked nucleosides, wherein the gap segment is positioned immediately adjacent to and between the 5' wing segment and the 3' wing segment and wherein each nucleoside of each wing segment comprises a modified sugar. In certain embodiments, the modified oligonucleotide further comprises at least one phosphorothioate internucleoside linkage.

In certain embodiments, provided are methods or uses wherein the animal is human.

In certain embodiments, the administering of a TMPRSS6 inhibitor reduces accumulation of iron in the animal. In certain embodiments, the TMPRSS6 inhibitor increases hepcidin expression levels. In other embodiments, the TMPRSS6 inhibitor decreases the percentage of saturation of transferrin.

In certain embodiments, the compound is co-administered with one or more second agent(s). In certain embodiments the second agent is an iron chelator or a hepcidin agonist. In further embodiments, the iron chelator includes FBS0701 (FerroKin), Exjade, Desferal or Deferiprone. In certain embodiments, the second agent is a second antisense compound. In further embodiments, the second antisense compound targets TMPRSS6. In other embodiments, the second antisense compound targets a non-TMPRSS6 compound. In other embodiments, the TMPRSS6 inhibitor is administered before, during or after phlebotomy therapy.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound can be "antisense" to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to TMPRSS6 nucleic acid is 10 to 30 nucleotides in length. In other words, antisense compounds are from 10 to 30 linked nucleobases. In other embodiments, the antisense compound comprises a modified oligonucleotide consisting of 8 to 80, 10 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In some embodiments, the antisense compound is an antisense oligonucleotide.

In certain embodiments, the antisense compound comprises a shortened or truncated modified oligonucleotide. The shortened or truncated modified oligonucleotide can have a single nucleoside deleted from the 5' end (5' truncation), the central portion or alternatively from the 3' end (3' truncation). A shortened or truncated oligonucleotide can have two or more nucleosides deleted from the 5' end, two or more nucleosides deleted from the central portion or alternatively can have two or more nucleosides deleted from the 3' end. Alternatively, the deleted nucleosides can be dispersed throughout the modified oligonucleotide, for example, in an antisense compound having one or more nucleoside deleted from the 5' end, one or more nucleoside deleted from the central portion and/or one or more nucleoside deleted from the 3' end.

When a single additional nucleoside is present in a lengthened oligonucleotide, the additional nucleoside can be located at the 5' end, 3' end or central portion of the oligonucleotide. When two or more additional nucleosides are present, the added nucleosides can be adjacent to each other, for example, in an oligonucleotide having two nucleosides added to the 5' end (5' addition), to the 3' end (3' addition) or the central portion, of the oligonucleotide. Alternatively, the added nucleoside can be dispersed throughout the antisense compound, for example, in an oligonucleotide having one or more nucleoside added to the 5' end, one or more nucleoside added to the 3' end, and/or one or more nucleoside added to the central portion.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a TMPRSS6 nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound can optionally serve as a substrate for the cellular endonuclease RNase H, which cleaves the RNA strand of a RNA:DNA duplex.

Antisense compounds having a gapmer motif are considered chimeric antisense compounds. In a gapmer an internal region having a plurality of nucleotides that supports RNase H cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer can in some embodiments include β-D-ribonucleosides, β-D-deoxyribonucleosides, 2'-modified nucleosides (such 2'-modified nucleosides can include 2'-MOE, and 2'-O—CH$_3$, among others), and bicyclic sugar modified nucleosides (such bicyclic sugar modified nucleosides can include those having a 4'-(CH2) n-O-2' bridge, where n=1 or n=2). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same; in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6, 5-8-5, 1-8-1, 2-6-2, 6-8-6, 5-8-5, 1-8-1, 2-6-2, 2-13-2, 1-8-2, 2-8-3, 3-10-2, 1-18-2, or 2-18-2.

In certain embodiments, the antisense compound as a "wingmer" motif, having a wing-gap or gap-wing configuration, i.e. an X—Y or Y—Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

Target Nucleic Acids, Target Regions and Nucleotide Sequences

Nucleotide sequences that encode TMPRSS6 include, without limitation, the following: GENBANK Accession No. NM_027902.2 (incorporated herein as SEQ ID NO: 1), GENBANK Accession NM_153609.2 (incorporated herein as SEQ ID NO: 2), the complement of GENBANK Accession NT_011520.12 truncated from 16850000 to 16891250 (incorporated herein as SEQ ID NO: 3), GENBANK Accession CR456446.1 (incorporated herein as SEQ ID NO: 4), GENBANK Accession No. BC039082.1 (incorporated herein as SEQ ID NO: 5), GENBANK Accession No. AY358398.1 (incorporated herein as SEQ ID NO: 6), or GENBANK Accession No. DB081153.1 (incorporated herein as SEQ ID NO: 7).

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for TMPRSS6 can be obtained by accession number from sequence databases such as NCBI and such information is incorporated herein by reference. In certain embodiments, a target region may encompass the sequence from a 5' target site of one target segment within the target region to a 3' target site of another target segment within the target region.

In certain embodiments, a "target segment" is a smaller, sub-portion of a target region within a nucleic acid. For example, a target segment can be the sequence of nucleotides of a target nucleic acid to which one or more antisense compound is targeted. "5' target site" refers to the 5'-most nucleotide of a target segment. "3' target site" refers to the 3'-most nucleotide of a target segment.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in TMPRSS6 mRNA levels are indicative of inhibition of TMPRSS6 expression. Reductions in levels of a TMPRSS6 protein are also indicative of inhibition of TMPRSS6 expression. Further, phenotypic changes are indicative of inhibition of TMPRSS6 expression. For example, an increase in hepcidin expression levels can be indicative of inhibition of TMPRSS6 expression. In another example, a decrease in iron accumulation in tissues can be indicative of inhibition of TMPRSS6 expression. In another example, an increase in the percentage of saturation of transferrin can be indicative of inhibition of TMPRSS6 expression.

Hybridization

In some embodiments, hybridization occurs between an antisense compound disclosed herein and a TMPRSS6 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrook and Russell, Molecular Cloning: A Laboratory Manual, $3^{rd}$ Ed., 2001). In certain embodiments, the antisense compounds provided herein are specifically hybridizable with a TMPRSS6 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a TMPRSS6 nucleic acid).

Non-complementary nucleobases between an antisense compound and a TMPRSS6 nucleic acid may be tolerated provided that the antisense compound remains able to specifically hybridize to a target nucleic acid. Moreover, an antisense compound may hybridize over one or more segments of a TMPRSS6 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a TMPRSS6 nucleic acid, a target region, target segment, or specified portion thereof. Percent complementarity of an antisense compound with a target nucleic acid can be determined using routine methods. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention.

Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a TMPRSS6 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a TMPRSS6 nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a TMPRSS6 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occuring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a TMPRSS6 nucleic acid comprise one or more modified internucleoside linkages. In certain embodiments, the modified internucleoside linkages are phosphorothioate linkages.

In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US 2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C)

ethyleneoxy (4'-(CH₂)₂—O-2') BNA, (D) aminooxy (4'-CH₂—O—N(R)-2') BNA, (E) oxyamino (4'-CH₂—N(R)—O-2') BNA, and (F) methyl(methyleneoxy) (4'-CH(CH₃)—O-2') BNA, (G) methylene thio (4'-CH₂—S-2') BNA, (H) methylene-amino (4'-CH₂—N(R)-2') BNA, (I) methyl carbocyclic (4'-CH₂—CH(CH₃)-2') BNA, and (J) propylene carbocyclic (4'-(CH₂)₃-2') BNA as depicted below.

(A)
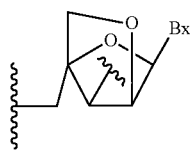

(B)
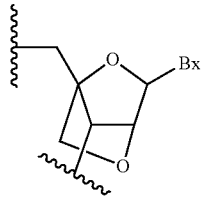

(C)
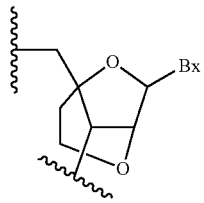

(D)
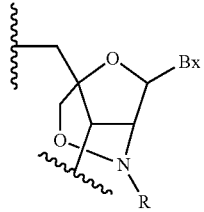

(E)
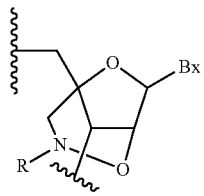

(F)
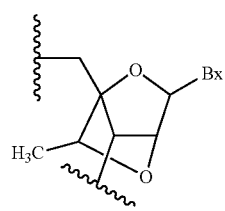

(G)
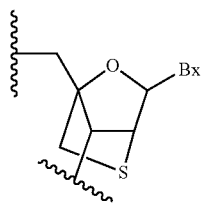

(H)
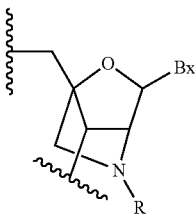

(I)
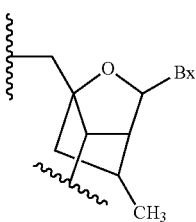

(J)
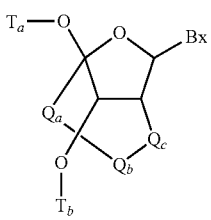

wherein Bx is the base moiety and R is independently H, a protecting group or $C_1$-$C_{12}$ alkyl.

In certain embodiments, bicyclic nucleosides are provided having Formula I:

I
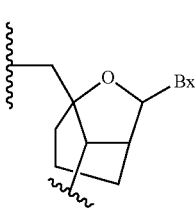

wherein:

Bx is a heterocyclic base moiety;

-$Q_a$-$Q_b$-$Q_c$- is —CH₂—N($R_c$)—CH₂—, —C(=O)—N($R_c$)—CH₂—, —CH₂—O—N($R_c$)—, —CH₂—N($R_c$)—O— or —N($R_c$)—O—CH₂;

$R_c$ is $C_1$-$C_{12}$ alkyl or an amino protecting group; and $T_a$ and $T_b$ are each, independently, H, a hydroxyl protecting group, a conjugate group, a reactive phosphorus group, a phosphorus moiety or a covalent attachment to a support medium.

In certain embodiments, bicyclic nucleosides are provided having Formula II:

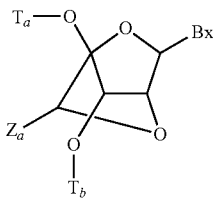

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

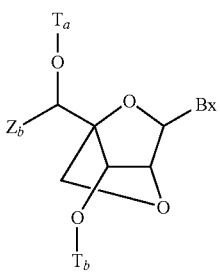

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

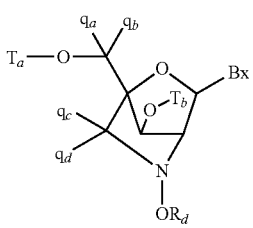

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

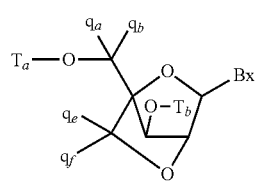

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, $CN$, $C(=O)OJ_j$, $C(=O)NJ_jJ_k$, $C(=O)J_j$, $O—C(=O)—NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

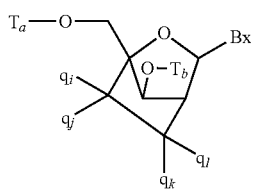

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta.*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

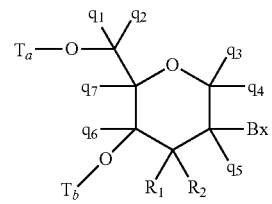

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$," or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a TMPRSS6 nucleic acid comprise one or more modified nucleobases. In certain embodiments, gap-widened antisense oligonucleotides targeted to a TMPRSS6 nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a TMPRSS6 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a TMPRSS6 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

A prodrug can include the incorporation of additional nucleosides at one or both ends of an antisense compound which are cleaved by endogenous nucleases within the body, to form the active antisense compound.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of TMPRSS6 or the prevention, reduction, amelioration or slowing the progression of a disease, disorder or condition associated with TMPRSS6.

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 µg to 100 mg per kg of body weight, or within a range of 0.001 mg to 1000 mg dosing, and may be given once or more daily, weekly, monthly or yearly, or even once every 2 to 20 years. Following successful treatment, it may be desirable to have the patient undergo maintenance therapy to prevent the recurrence of the disease state, wherein the oligonucleotide is administered in maintenance doses, ranging from 0.01 µg to 100 mg per kg of body weight, once or more daily, to once every 20 years or ranging from 0.001 mg to 1000 mg dosing.

Administration

The compounds or pharmaceutical compositions of the present invention can be administered in a number of ways depending upon whether local or systemic treatment is desired and upon the area to be treated. Administration can be oral, inhaled or parenteral.

In certain embodiments, the compounds and compositions as described herein are administered parenterally. Parenteral administration includes intravenous, intra-arterial, subcutaneous, intraperitoneal or intramuscular injection or infusion; or intracranial, e.g., intrathecal or intraventricular, administration.

In certain embodiments, parenteral administration is by infusion. Infusion can be chronic or continuous or short or intermittent. In certain embodiments, infused pharmaceutical agents are delivered with a pump.

In certain embodiments, parenteral administration is by injection. The injection can be delivered with a syringe or a pump. In certain embodiments, the injection is a bolus injection. In certain embodiments, the injection is administered directly to a tissue or organ.

In certain embodiments, formulations for parenteral, intrathecal or intraventricular administration can include sterile aqueous solutions which can also contain buffers, diluents and other suitable additives such as, but not limited to, penetration enhancers, carrier compounds and other pharmaceutically acceptable carriers or excipients.

In certain embodiments, formulations for oral administration of the compounds or compositions can include, but is not limited to, pharmaceutical carriers, excipients, powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In certain embodiments, oral formulations are those in which compounds provided herein are administered in conjunction with one or more penetration enhancers, surfactants and chelators.

In certain embodiments, administration includes pulmonary administration. In certain embodiments, pulmonary administration comprises delivery of aerosolized oligonucleotide to the lung of a subject by inhalation. Following inhalation by a subject of aerosolized oligonucleotide, oligonucleotide distributes to cells of both normal and inflamed lung tissue, including alveolar macrophages, eosinophils, epithelium, blood vessel endothelium, and bronchiolar epithelium. A suitable device for the delivery of a pharmaceutical composition comprising a modified oligonucleotide includes, but is not limited to, a standard nebulizer device. Additional suitable devices include dry powder inhalers or metered dose inhalers.

In certain embodiments, pharmaceutical compositions are administered to achieve local rather than systemic exposures. For example, pulmonary administration delivers a pharmaceutical composition to the lung, with minimal systemic exposure.

Additional suitable administration routes include, but are not limited to, rectal, transmucosal, intestinal, enteral, topical, suppository, intrathecal, intraventricular, intraperitoneal, intranasal, intraocular, intramuscular, intramedullary, and intratumoral.

Conjugated Antisense Compounds

In certain embodiments, the compounds of the invention can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

In certain embodiments, antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3' terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of TMPRSS6 nucleic acids can be tested in vitro in a variety of cell types. Cell types used for such analyses are available from commercial vendors (e.g.

American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrook and Russell in *Molecular Cloning. A Laboratory Manual*. Third Edition. Cold Spring Harbor laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrook and Russell in *Molecular Cloning. A Laboratory Manual*. Third Edition. Cold Spring Harbor laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrook and Russell in *Molecular Cloning. A Laboratory Manual*. Third Edition. Cold Spring Harbor laboratory Press, Cold Spring Harbor, N.Y. 2001). Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art (Sambrook and Russell, Molecular Cloning: A Laboratory Manual, $3^{rd}$ Ed., 2001). RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a TMPRSS6 nucleic acid can be assayed in a variety of ways known in the art (Sambrook and Russell, Molecular Cloning: A Laboratory Manual, $3^{rd}$ Ed., 2001). For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a TMPRSS6 nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of TMPRSS6 nucleic acids can be assessed by measuring TMPRSS6 protein levels. Protein levels of TMPRSS6 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrook and Russell, Molecular Cloning: A Laboratory Manual, $3^{rd}$ Ed., 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of TMPRSS6 and produce phenotypic changes, such as, reduced accumulation of iron in the body. Testing can be performed in normal animals, or in experimental disease models. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency depends upon factors such as route of administration and animal body weight. In one embodiment, following a period of treatment with antisense oligonucleotides, RNA is isolated from liver tissue and changes in TMPRSS6 nucleic acid expression are measured. Changes in TMPRSS6 protein levels can also be measured. Changes in TMPRSS6 expression can be measured by determining the level of hepcidin expression, plasma levels of iron and percentage saturation of transferrin present in the animal.

Certain Indications

In certain embodiments, provided herein are methods of treating an individual comprising administering one or more pharmaceutical compositions of the present invention. In certain embodiments, the individual has or is at risk for an iron accumulation disease, disorder or condition. In certain embodiments, the individual is at risk for an iron accumulation disease, disorder or condition as described, supra. In certain embodiments the invention provides methods for prophylactically reducing TMPRSS6 expression in an individual. Certain embodiments include treating an individual in need thereof by administering to an individual a therapeutically effective amount of an antisense compound targeted to a TMPRSS6 nucleic acid.

In certain embodiments, administration of a therapeutically effective amount of an antisense compound targeted to a TMPRSS6 nucleic acid is accompanied by monitoring of TMPRSS6 levels in an individual, to determine an individual's response to administration of the antisense compound.

In certain embodiments, administration of a therapeutically effective amount of an antisense compound targeted to a TMPRSS6 nucleic acid is accompanied by monitoring the levels of hepcidin in an individual. In certain embodiments, administration of a therapeutically effective amount of an antisense compound targeted to a TMPRSS6 nucleic acid is accompanied by monitoring the levels of iron in an individual. In certain embodiments, administration of a therapeutically effective amount of an antisense compound targeted to a TMPRSS6 nucleic acid is accompanied by evaluating the percentage saturation of transferrin in an individual. An individual's response to administration of the antisense compound is used by a physician to determine the amount and duration of therapeutic intervention.

In certain embodiments, pharmaceutical compositions comprising an antisense compound targeted to TMPRSS6 are used for the preparation of a medicament for treating a patient suffering or susceptible to an iron accumulation disease, disorder or condition.

In certain embodiments, the methods described herein include administering a compound comprising a modified oligonucleotide having an 8, 9, 10, 11, 12, 13, 14, 15, 16, 17, 18, 19 or 20 contiguous nucleobase portion complementary to a TMPRSS6 nucleic acid.

Certain Combination Therapies

In certain embodiments, a first agent comprising a modified oligonucleotide provided herein is co-administered with one or more secondary agents. In certain embodiments, such second agents are designed to treat the same iron accumulation disease, disorder or condition as the first agent described herein. In certain embodiments, such second agents are designed to treat a different disease, disorder, or condition as the first agent described herein. In certain embodiments, such second agents are designed to treat an undesired side effect of one or more pharmaceutical compositions as described herein. In certain embodiments, such first agents are designed to treat an undesired side effect of a second agent. In certain embodiments, second agents are co-administered with the first agent to treat an undesired effect of the first agent. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, second agents include, but are not limited to, nucleic acid compounds. Such nucleic acid compounds can include a siRNA, a ribozyme or an antisense compound targeting TMPRSS6 or another target.

In certain embodiments, second agents include, but are not limited to, non-antisense compounds such as iron chelators, transferrin, bone morphogenetic proteins 6 (BMP6), hepcidin agonists, stem cells or fetal hemoglobin (HbF)-raising agents. In further embodiments, iron chelators are selected from, but not limited to, FBS0701 (FerroKin), Exjade, Desferal, and Deferiprone. In certain embodiments, HBF-raising agents include 5-hydroxyl urea, short chain fatty acid (SCFA) derivatives (e.g., HQK1001), DNA methyltransferase inhibitors (e.g., decitabine) or histone deacetylase (HDAC) inhibitors (e.g., Zolina, Panobinostat). In certain embodiments, the second agent is administered prior to administration of the first agent. In certain embodiments, the second agent is administered following administration of the first agent. In certain embodiments the second agent is administered at the same time as the first agent. In certain embodiments the dose of a co-administered second agent is the same as the dose that would be administered if the second agent was administered alone. In certain embodiments the dose of a co-administered second agent is lower than the dose that would be administered if the second agent was administered alone. In certain embodiments the dose of a co-administered second agent is greater than the dose that would be administered if the second agent was administered alone. In certain embodiments, the first agent is administered at the same time as phlebotomy therapy. In certain embodiments, the first agent is administered prior to phlebotomy therapy. In certain embodiments, the first agent is administered following phlebotomy therapy. In certain embodiments, the frequency of phlebotomy is decreased. In certain embodiments, the length of time required for phlebotomy is decreased.

Advantages of the Invention

Provided herein, for the first time, are methods and compositions for the modulation of TMPRSS6 that can treat, prevent and/or ameliorate an iron accumulation disease. In a particular embodiment, provided are TMPRSS6 inhibitors such as antisense oligonucleotides (oligonucleotides targeting a nucleic acid encoding TMPRSS6 protein) to ameliorate an iron accumulation disorder such as hemochromatosis, polycythemia or thalassemia.

Targeting TMPRSS6 with TMPRSS6 specific inhibitors as described herein has several positive effects including, but not limited to: (a) increasing hepcidin levels, (b) preventing excessive iron absorption and iron overload, (c) increasing serum transferrin concentrations, which will further decrease transferrin saturation and hemichrome formation, (d) safely storing excess iron in macrophages and (e) decreasing transferrin saturation, leading to a decreased iron supply for erythropoiesis.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: In Vivo Antisense Inhibition of Murine Type II Transmembrane Serine Protease 6 (TMPRSS6)

Several antisense oligonucleotides were designed targeting murine TMPRSS6 mRNA (GENBANK Accession No. NM_027902.2, incorporated herein as SEQ ID NO: 1). The target start sites and sequences of each oligonucleotide are presented in Table 1. The chimeric antisense oligonucleotides in Table 1 were designed as 5-10-5 MOE gapmers. The gapmers are 20 nucleosides in length, wherein the central gap segment is comprised of ten 2'-deoxynucleosides and is flanked on both sides (in the 5' and 3' directions) by wings comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

TABLE 1

Gapmers targeting murine TMPRSS6

| ISIS No | Sequence | Target Start Site | SEQ ID NO |
| --- | --- | --- | --- |
| 537402 | AGGCCTTCCGGGTCCACCTC | 795 | 8 |
| 537450 | TTTCTTTCCTACAGAGACCC | 2933 | 9 |
| 537451 | AGCCTTGATAGAGGCACCTT | 3001 | 10 |
| 537452 | GCTTAGAGTACAGCCCACTT | 3044 | 11 |
| 537480 | TCACCAGGCCTTCCGGGTCC | 800 | 12 |
| 537524 | AGGCATCCTAACCACCAGCT | 2789 | 13 |

Treatment

Groups of four C57BL/6 mice each were injected with 25 mg/kg of ISIS 537402, ISIS 537450, ISIS 537451, ISIS 537452, ISIS 537480, or ISIS 537524 twice weekly for 4 weeks. A group of four mice each were injected with 25 mg/kg of control oligonucleotide, ISIS 141923 (CCTTC-CCTGAAGGTTCCTCC, designated herein as SEQ ID NO: 14; a 5-10-5 MOE gapmer with no known murine target), twice weekly for 4 weeks. A control group of mice was injected with phosphate buffered saline (PBS) twice weekly for 4 weeks. Mice were sacrificed two days after the final dose.

RNA Analysis

RNA was extracted from liver tissue for real-time PCR analysis of TMPRSS6, using primer probe set RTS3481 (forward sequence ATTCCACGCTGGGCTGTTAT, designated herein as SEQ ID NO: 15; reverse sequence CTG-GTCAGGCCCCTTCAA, designated herein as SEQ ID NO: 16; probe sequence TGAACCCAGGCCAGGTCCTCCC, designated herein as SEQ ID NO: 17). RT-PCR analysis of hepcidin was also conducted, using primer probe set RTS1777 (forward sequence TGCAGAAGA-GAAGGAAGAGAGACA, designated herein as SEQ ID NO: 18; reverse sequence CACACTGGGAATTGTTACA-GCATT, designated herein as SEQ ID NO: 19; probe sequence CAACTTCCCCATCTGCATCTTCTGCTGT, designated herein as SEQ ID NO: 20). The mRNA levels were normalized using RIBOGREEN®. As shown in Table 2, most of the antisense oligonucleotides achieved reduction of murine TMPRSS6 over the PBS control. Results are presented as percent inhibition of TMPRSS6, relative to control. As shown in Table 3, most of the antisense oligonucleotides achieved increase in murine hepcidin levels compared to the PBS control. Results are presented as percent change of hepcidin levels, relative to the control.

TABLE 2

Percent inhibition of murine TMPRSS6 mRNA levels in C57BL/6 mice

| ISIS NO | % inhibition of TMPRSS6 |
|---|---|
| 537402 | 65 |
| 537450 | 80 |
| 537451 | 39 |
| 537452 | 86 |
| 537480 | 60 |
| 537524 | 90 |
| 141923 | 0 |

TABLE 3

Percent increase in murine hepcidin mRNA levels in C57BL/6 mice

| ISIS NO | % hepcidin |
|---|---|
| 537402 | +28 |
| 537450 | +113 |
| 537451 | −7 |
| 537452 | +201 |
| 537480 | +13 |
| 537524 | +181 |
| 141923 | −38 |

Effect on Iron Levels

Serum iron levels were measured using an automated clinical chemistry analyzer (Hitachi Olympus AU400e, Melville, N.Y.) (Siek, G. et al., Clin. Chem. 48: 161-166, 2002). The results are presented in Table 4, expressed as µg/dL. The results indicate that several of the ISIS oligonucleotides reduced iron levels.

TABLE 4

Iron levels (µg/dL) in C57BL/6 mice

| | Iron (µg/dL) |
|---|---|
| PBS | 161 |
| ISIS 537402 | 148 |
| ISIS 537450 | 94 |
| ISIS 537451 | 161 |
| ISIS 537452 | 82 |
| ISIS 537480 | 135 |
| ISIS 537524 | 104 |
| ISIS 141923 | 144 |

Body and Organ Weights

The effect of antisense inhibition of TMPRSS6 on the overall health of the animals, as demonstrated by changes in body and organ weights, was assessed. As shown in Table 5, there was no significant change in the body weights of the mice treated with antisense oligonucleotide, compared to that of the PBS control. Similarly, as shown in Table 6, there was negligible change in organ weights of the mice treated with antisense oligonucleotide, compared to that of the PBS control.

TABLE 5

Body weights (g) of C57BL/6 mice

| | Body weight (g) |
|---|---|
| PBS | 24.6 |
| ISIS 537402 | 26.1 |
| ISIS 537450 | 22.7 |
| ISIS 537451 | 26.0 |
| ISIS 537452 | 25.2 |
| ISIS 537480 | 26.4 |
| ISIS 537524 | 27.2 |
| ISIS 141923 | 26.8 |

TABLE 6

Organ weights (g) of C57BL/6 mice

| | Liver | Kidney | Spleen |
|---|---|---|---|
| PBS | 1.4 | 0.08 | 0.34 |
| ISIS 537402 | 1.6 | 0.09 | 0.31 |
| ISIS 537450 | 1.5 | 0.09 | 0.33 |
| ISIS 537451 | 1.6 | 0.08 | 0.33 |
| ISIS 537452 | 1.6 | 0.09 | 0.34 |
| ISIS 537480 | 1.7 | 0.08 | 0.34 |
| ISIS 537524 | 1.6 | 0.11 | 0.35 |
| ISIS 141923 | 1.6 | 0.09 | 0.31 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.) (Nyblom, H. et al., Alcohol & Alcoholism 39: 336-339, 2004; Tietz N W (Ed): Clinical Guide to Laboratory Tests, 3rd ed. W. B. Saunders, Philadelphia, Pa., 1995). Plasma concentrations of ALT (alanine transaminase) and AST (aspartate transaminase) were measured and the results are presented in Table 7 expressed in IU/L. Several of the ISIS oligonucleotides were considered tolerable in the mice, as demonstrated by their liver transaminase profile.

TABLE 7

ALT and AST levels (IU/L) of C57BL/6 mice

| | ALT | AST |
|---|---|---|
| PBS | 40 | 59 |
| ISIS 537402 | 42 | 63 |
| ISIS 537450 | 49 | 77 |
| ISIS 537451 | 54 | 67 |
| ISIS 537452 | 38 | 67 |
| ISIS 537480 | 35 | 58 |
| ISIS 537524 | 219 | 180 |
| ISIS 141923 | 60 | 83 |

Kidney Function

To evaluate the effect of ISIS oligonucleotides on renal function, plasma concentrations of BUN were measured using an automated clinical chemistry analyzer (Hitachi Olympus AU400e, Melville, N.Y.) (Nyblom, H. et al., Alcohol & Alcoholism 39: 336-339, 2004; Tietz N W (Ed): Clinical Guide to Laboratory Tests, 3rd ed. W. B. Saunders, Philadelphia, Pa., 1995). The results are presented in Table 8 expressed in mg/dL. Several of the ISIS oligonucleotides were considered tolerable in the mice, as demonstrated by their plasma BUN profile.

TABLE 8

BUN levels (mg/dL) of C57BL/6 mice

|  | BUN |
| --- | --- |
| PBS | 41 |
| ISIS 537402 | 43 |
| ISIS 537450 | 42 |
| ISIS 537451 | 47 |
| ISIS 537452 | 37 |
| ISIS 537480 | 34 |
| ISIS 537524 | 40 |
| ISIS 141923 | 35 |

Example 2: Effect of Dose-Dependent Antisense Inhibition of Murine TMPRSS6

The effect of treatment with several dose concentrations of ISIS 537450 and ISIS 537452 was assessed in C57BL/6 wildtype mice.

Treatment

Three groups of four C57BL/6 mice each were injected with 25 mg/kg, 50 mg/kg, or 100 mg/kg of ISIS 537450, weekly for 4 weeks. Three groups of four C57BL/6 mice each were injected with 25 mg/kg, 50 mg/kg, or 100 mg/kg of ISIS 537452, weekly for 4 weeks. A group of 4 mice each were injected with 50 mg/kg of control oligonucleotide, ISIS 141923 (SEQ ID NO: 14), weekly for 4 weeks. A control group of mice was injected with phosphate buffered saline (PBS) administered weekly for 4 weeks. Mice were sacrificed two days after the final dose.

RNA Analysis

RNA was extracted from liver tissue for real-time PCR analysis of TMPRSS6, using primer probe set RTS3481. RT-PCR analysis of hepcidin was also conducted, using primer probe set RTS1777. The mRNA levels were normalized using RIBOGREEN®. As shown in Table 9, the antisense oligonucleotides achieved dose-dependent reduction of murine TMPRSS6 over the PBS control. Results are presented as percent inhibition of TMPRSS6, relative to control. As shown in Table 10, the antisense oligonucleotides achieved dose-dependent increase of murine hepcidin levels compared to the PBS control. Results are presented as percent increase in hepcidin, relative to control.

TABLE 9

Percent inhibition of murine TMPRSS6 mRNA levels in C57BL/6 mice

|  | Dose (mg/kg/wk) | % inhibition |
| --- | --- | --- |
| ISIS 537450 | 25 | 45 |
|  | 50 | 76 |
|  | 100 | 90 |
| ISIS 537452 | 25 | 56 |
|  | 50 | 88 |
|  | 100 | 100 |
| ISIS 141923 | 100 | 27 |

TABLE 10

Percent increase in murine hepcidin mRNA levels in C57BL/6 mice

|  | Dose (mg/kg/wk) | % increase |
| --- | --- | --- |
| ISIS 537450 | 25 | 28 |
|  | 50 | 110 |
|  | 100 | 372 |
| ISIS 537452 | 25 | 55 |
|  | 50 | 268 |
|  | 100 | 349 |
| ISIS 141923 | 100 | 109 |

Effect on Iron Levels

Unsaturated iron-binding capacity (UIBC) is frequently used along with a serum iron test to evaluate iron overload in hemochromatosis patients (Yamanishi, H. et al., Clin. Chem. 49: 175-178, 2003). These two tests are used to calculate the transferrin saturation, a more useful indicator of iron status than just iron or UIBC alone (Adams, P. C. et al., N Engl. J. Med. 352: 1769-1778, 2005). Iron levels and unsaturated iron binding capacity of the transferrin molecules were measured using an automated clinical chemistry analyzer (Hitachi Olympus AU400e, Melville, N.Y.) (Siek, G. et al., Clin. Chem. 48: 161-166, 2002). The results for iron levels, transferrin levels and percentage saturation of transferrin are presented in Tables 11 and 12, and indicate that treatment with ISIS oligonucleotides reduced iron levels and percent saturation of transferrin and increased transferrin levels.

TABLE 11

Iron levels of C57BL/6 mice

|  | Dose (mg/kg/wk) | Iron (µg/dL) |
| --- | --- | --- |
| PBS | — | 109 |
| ISIS 537450 | 25 | 102 |
|  | 50 | 56 |
|  | 100 | 38 |
| ISIS 537452 | 25 | 93 |
|  | 50 | 53 |
|  | 100 | 44 |
| ISIS 141923 | 100 | 87 |

TABLE 12

Percent saturation of transferrin and transferrin levels in C57BL/6 mice

|  | Dose (mg/kg/wk) | Transferrin saturation (%) | Transferrin (ng/mL) |
| --- | --- | --- | --- |
| PBS | — | 35 | 122 |
| ISIS 537450 | 25 | 28 | 136 |
|  | 50 | 14 | 151 |
|  | 100 | 9 | 159 |
| ISIS 537452 | 25 | 25 | 142 |
|  | 50 | 11 | 164 |
|  | 100 | 8 | 183 |
| ISIS 141923 | 100 | 23 | 144 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.) (Nyblom, H. et al., Alcohol & Alcoholism 39: 336-339, 2004; Tietz N W (Ed): Clinical Guide to Laboratory Tests, 3rd ed. W. B. Saunders, Philadelphia, Pa., 1995). Plasma concentrations of ALT (alanine transaminase) and AST (aspartate transaminase)

were measured and the results are presented in Table 13 expressed in IU/L. The ISIS oligonucleotides targeting TMPRSS6 were considered tolerable in the mice, as demonstrated by their liver transaminase profile.

TABLE 13

ALT and AST levels (IU/L) of C57BL/6 mice

|  | Dose (mg/kg/wk) | ALT | AST |
|---|---|---|---|
| PBS | — | 45 | 79 |
| ISIS 537450 | 25 | 50 | 95 |
|  | 50 | 22 | 62 |
|  | 100 | 24 | 66 |
| ISIS 537452 | 25 | 17 | 38 |
|  | 50 | 54 | 60 |
|  | 100 | 38 | 76 |
| ISIS 141923 | 100 | 112 | 172 |

Kidney Function

To evaluate the effect of ISIS oligonucleotides on renal function, plasma concentrations of BUN were measured using an automated clinical chemistry analyzer (Hitachi Olympus AU400e, Melville, N.Y.) (Nyblom, H. et al., Alcohol & Alcoholism 39: 336-339, 2004; Tietz N W (Ed): Clinical Guide to Laboratory Tests, 3rd ed. W. B. Saunders, Philadelphia, Pa., 1995). The results are presented in Table 14 expressed in mg/dL. The ISIS oligonucleotides targeting TMPRSS6 were considered tolerable in the mice, as demonstrated by their plasma BUN profile.

TABLE 14

BUN levels (mg/dL) of C57BL/6 mice

|  | Dose (mg/kg/wk) | BUN |
|---|---|---|
| PBS | — | 36 |
| ISIS 537450 | 25 | 32 |
|  | 50 | 33 |
|  | 100 | 32 |
| ISIS 537452 | 25 | 32 |
|  | 50 | 32 |
|  | 100 | 35 |
| ISIS 141923 | 100 | 32 |

Example 3: Effect of Antisense Inhibition of Murine TMPRSS6 in HFE Knockout Mice The effect of treatment of antisense oligonucleotide targeting murine TMPRSS6 was assessed in HFE$^{-/-}$ mice. HFE$^{-/-}$ mice have profound differences in parameters of iron homeostasis compared to wild-type littermates. Fasting transferrin saturation is significantly elevated and hepatic iron concentrations are significantly higher than control mice. The HFE knockout mice are therefore regarded as a standard model of hereditary hemochromatosis (Zhou, X. Y. et al., Proc. Natl. Acad. Sci. 1998. 95: 2492-2497).

ISIS 537450 (TTTCTTTCCTACAGAGACCC; SEQ ID NO: 9) is a 5-10-5 MOE gapmer, 20 nucleosides in length, wherein the central gap segment is comprised of ten 2'-deoxynucleosides and is flanked on both sides (in the 5' and 3' directions) by wings comprising five nucleosides each. Each nucleoside in the 5' wing segment and each nucleoside in the 3' wing segment has a 2'-MOE modification. The internucleoside linkages throughout the gapmer are phosphorothioate (P=S) linkages. All cytosine residues throughout the gapmer are 5-methylcytosines. ISIS 537450 targets murine TMPRSS6 mRNA (GENBANK Accession No. NM_027902.2, incorporated herein as SEQ ID NO: 1) with a target start site of 2933.

The effect of treatment of the mice with ISIS 537450 on TMPRSS6 mRNA and iron levels was assessed.

Treatment

A group of 12 male and female HFE$^{-/-}$ mice were injected with 100 mg/kg of ISIS 537450 weekly for 6 weeks. A control group of 11 male and female HFE$^{-/-}$ mice was injected with PBS weekly for 6 weeks. The mice were provided with normal chow during the study period. The mice were euthanized 2 days after the final dose of antisense oligonucleotide or PBS.

RNA Analysis

RNA was extracted from liver tissue for real-time PCR analysis of TMPRSS6, using primer probe set RTS3481 (forward sequence ATTCCACGCTGGGCTGTTAT, designated herein as SEQ ID NO: 15; reverse sequence CTGGTCAGGCCCCTTCAA, designated herein as SEQ ID NO: 16; probe sequence TGAACCCAGGCCAGGTCCTCCC, designated herein as SEQ ID NO: 17). RT-PCR analysis of hepcidin was also conducted, using primer probe set RTS1777 (forward sequence TGCAGAAGAGAAGGAAGAGAGACA, designated herein as SEQ ID NO: 18; reverse sequence CACACTGGGAATTGTTACAGCATT, designated herein as SEQ ID NO: 19; probe sequence CAACTTCCCCATCTGCATCTTCTGCTGT, designated herein as SEQ ID NO: 20). The mRNA levels were normalized using RIBOGREEN®. Treatment with ISIS 537450 achieved 88% reduction of murine TMPRSS6 over the PBS control. Treatment with ISIS 537450 also achieved 152% increase of murine hepcidin levels compared to the PBS control.

Effect on Iron Levels

Iron levels were measured using an automated clinical chemistry analyzer (Hitachi Olympus AU400e, Melville, N.Y.) (Siek, G. et al., Clin. Chem. 48: 161-166, 2002). The results for transferrin levels, iron levels and percentage saturation of transferrin are presented in Table 15, and indicate that treatment with ISIS oligonucleotides increased transferrin levels and reduced iron levels and percent saturation of transferrin. In comparison, iron levels in untreated wildtype mice (C57BL/6) shown supra are usually about 110 µg/dL, transferrin levels are about 122 ng/mL and the transferrin saturation is about 35%. Hence, antisense inhibition of TMPRSS6 in this model resulted in improvement of iron levels, transferrin levels and transferrin saturation levels close to that found in wildtype mice.

The iron levels in the liver and spleen were measured by Exova (Santa Fe Springs, Calif.). The data is presented in Table 16. The results indicate that antisense inhibition of TMPRSS6 resulted in a decrease in hepatic iron accumulation and increase in iron retention in the macrophages of the HFE$^{-/-}$ mice. The reduction of iron from the liver tissue and the simultaneous absorption of unbound serum iron by macrophages indicate that antisense inhibition of TMPRSS6 in this model results in the amelioration of iron overload in tissues (Nemeth, E. et al., Science. 2004. 306: 2090-3).

TABLE 15

Serum iron levels, transferrin saturation and transferrin levels in HFE$^{-/-}$ mice

|  | Serum iron (μg/dL) | Transferrin saturation (%) | Transferrin (ng/mL) |
|---|---|---|---|
| PBS | 318 | 93 | 132 |
| ISIS 537450 | 142 | 26 | 183 |

TABLE 16

Iron levels in liver and macrophages of HFE$^{-/-}$ mice (μg/g tissue)

|  | Liver | Macrophages |
|---|---|---|
| PBS | 388 | 468 |
| ISIS 537450 | 256 | 683 |

Example 4: Effect of Antisense Inhibition of Murine TMPRSS6 in th3/+ Mice

The th3/+ mice model, a model of β-thalassemia, harbors a heterozygous deletion of β$^{minor}$ and β$^{major}$ genes (Yang, B. et al., Proc. Natl. Acad. Sci. U.S.A. 1995. 92: 11608-12; Ciavetta, D. J. et al., Proc. Natl. Acad. Sci. U.S.A. 1995. 92: 9259-63) and exhibits features comparable to those of patients affected by β-thalassemia intermedia (TI). The effect of treatment with an antisense oligonucleotide targeting murine TMPRSS6 was assessed in th3/+ mice.

ISIS 537452 (GCTTAGAGTACAGCCCACTT; SEQ ID NO: 11) is a 5-10-5 MOE gapmer, 20 nucleosides in length, wherein the central gap segment is comprised of ten 2'-deoxynucleosides and is flanked on both sides (in the 5' and 3' directions) by wings comprising five nucleosides each. Each nucleoside in the 5' wing segment and each nucleoside in the 3' wing segment has a 2'-MOE modification. The internucleoside linkages throughout the gapmer are phosphorothioate (P=S) linkages. All cytosine residues throughout the gapmer are 5-methylcytosines. ISIS 537452 targets murine TMPRSS6 mRNA (GENBANK Accession No. NM_027902.2, incorporated herein as SEQ ID NO: 1) with a target start site of 3044.

The effect of treatment of the mice with ISIS 537452 on various parameters in the mice was assessed.

Treatment

A group of equal number of male and female th3/+ mice, 10-15-week old, was injected with 100 mg/kg of ISIS 537452 weekly for 6 weeks. A control group of male and female th3/+ mice was injected with PBS weekly for 6 weeks. The mice were provided with normal chow during the study period. The mice were euthanized 2 days after the final dose of antisense oligonucleotide or PBS. The male and female groups were separately assessed.

RNA Analysis

RNA was extracted from liver tissue for real-time PCR analysis of TMPRSS6, using primer probe set RTS3481. RT-PCR analysis of hepcidin was also conducted, using primer probe set RTS1777. The mRNA levels were normalized using RIBOGREEN®. The data is presented in Table 17. The results indicate that ISIS 537452 significantly reduced liver TMPRSS6 levels. Antisense inhibition of TMPRSS6 levels was associated with a modest increase in absolute hepcidin expression in the th3/+ mice. However, when the expression of hepcidin was normalized by the liver iron concentration, the difference between the th3/+ untreated and treated ice mice was significant, corresponding to a 3.4 fold increase in males and a 2.0 fold increase in females. TMPRSS6 and hepcidin levels are expressed as a percentage of the male PBS control group.

TABLE 17

% change in th3/+ mice

|  | TMPRSS6 | Hepcidin |
|---|---|---|
| PBS-Female | +4 | +34 |
| ISIS 537452-Female | −85 | +64 |
| ISIS 537452-Male | −85 | +67 |

Serum Analysis

Iron and transferrin levels were measured using an automated clinical chemistry analyzer (Hitachi Olympus AU400e, Melville, N.Y.) (Siek, G. et al., Clin. Chem. 2002. 48: 161-166). Transferrin saturation was calculated. The data are presented in Table 18, and indicate that treatment with ISIS oligonucleotides reduced iron levels and percent saturation of transferrin.

Total Bilirubin levels were also measured by the same clinical chemistry analyzer. The data is also presented in Table 18. The results indicate that antisense inhibition of TMPRSS6 resulted in a decrease in total Bilirubin levels of the mice. Further, the majority of bilirubin was indirect bilirubin (data not shown) in the th3/+ mice, indicating that antisense inhibition decreased hemolysis.

TABLE 18

Serum parameters in th3/+ mice

|  |  | Iron levels (μg/dL) | Transferrin (ng/mL) | Transferrin saturation (%) | Total Bilirubin (mg/dL) |
|---|---|---|---|---|---|
| Male | PBS | 199 | 138 | 63 | 0.32 |
|  | ISIS 537452 | 134 | 172 | 26 | 0.16 |
| Female | PBS | 179 | 135 | 55 | 0.30 |
|  | ISIS 537452 | 111 | 164 | 20 | 0.15 |

Organ Analysis

Iron levels in the spleen and liver were measured by Diagnostic Center for Population and Animal Health (DCPAH) (Michigan State University, Lansing, Mich.). The data is presented in Tables 19 and 20. The results indicate that treatment with ISIS oligonucleotides reduced iron concentration in the liver. Measurement of the spleen weight indicated that antisense inhibition of TMPRSS6 also reduced spleen weight compared to the control groups. The spleen weight is expressed as a percentage to the weight measured in a group of mice at the start of the experiment. Pearl's Prussian Blue staining indicated that the iron in the spleen was predominantly localized in macrophages (data not shown) as expected by increased hepcidin expression. The reduction of iron from the liver tissue and the simultaneous absorption of unbound serum iron by macrophages indicate that antisense inhibition of TMPRSS6 in this model results in the amelioration of iron overload in tissues (Nemeth, E. et al., Science. 2004. 306: 2090-3).

Hence, antisense inhibition of TMPRSS6 reduces hepatic iron accumulation and splenomegaly associated with this mouse model (Pippard, M. J. et al., Lancet. 1979. 2: 819-21; Yang, B. et al., Proc. Natl. Acad. Sci. U.S.A. 1995. 92: 11608-12).

TABLE 19

Analysis of liver iron concentration in th3/+ mice

|  |  | Liver iron conc. (μg/dL) |
|---|---|---|
| Male | PBS | 605 |
|  | ISIS 537452 | 315 |
| Female | PBS | 1321 |
|  | ISIS 537452 | 816 |

TABLE 20

Analysis of spleen weight in th3/+ mice

|  |  | Relative spleen weight (%) |
|---|---|---|
| Male | PBS | 1.1 |
|  | ISIS 537452 | 0.1 |
| Female | PBS | 1.6 |
|  | ISIS 537452 | 0.1 |

Hematologic Analysis

Red blood cell (RBC) count, reticulocyte count, hemoglobin (HGB), and hematocrit (HCT) were measured at day 42 using an ADVIA120 hematology analyzer (Bayer, USA).

The data are presented in Table 21, and indicate that treatment with ISIS oligonucleotides increased RBC count, HGB and HCT levels, and decreased reticulocyte count (i.e., the number of reticulocytes as a percentage of the number of red blood cells). The increased RBC and decreased reticulocyte count indicates that antisense treatment improved RBC production.

Furthermore, treated th3/+ mice exhibited lower MCH and MCV values suggesting, as previously observed (Gardenghi et al., *J Clin Invest*, 2010, 120:4466-4477), that lower transferrin saturation levels were associated with decreased iron intake and hemichrome formation.

The results indicate that antisense inhibition of TMPRSS6 improved the anemic phenotype in this model.

TABLE 21

Analysis of the anemic phenotype in th3/+ mice

|  |  | RBC ($\times 10^6$ cells/μL) | Reticulocytes ($\times 10^5$ cells/μL) | HGB (g/dL) | HCT (g/dL) |
|---|---|---|---|---|---|
| Male | Day 0 | 8.3 | 1404 | 7.6 | 28.6 |
|  | Day 42 | 11.1 | 472 | 9.2 | 34.5 |
| Female | Day 0 | 8.5 | 1818 | 7.8 | 30.5 |
|  | Day 42 | 11.3 | 1029 | 10.0 | 36.5 |

What is claimed is:

1. A method comprising administering an antisense compound and a second agent to a subject, wherein the nucleobase sequence of the antisense compound is at least 90% complementary to a TMPRSS6 nucleic acid, wherein the antisense compound comprises a single-stranded, modified oligonucleotide, and wherein the second agent is an iron chelator.

2. The method of claim 1, wherein the iron chelator is FerroKin, Exjade, Desferal, or Deferiprone.

3. The method of claim 1, wherein the iron chelator is FerroKin.

4. The method of claim 1, wherein the iron chelator is Exjade.

5. The method of claim 1, wherein the iron chelator is Desferal.

6. The method of claim 1, wherein the iron chelator is Deferiprone.

7. The method of claim 1, wherein the subject has a disease, disorder and/or condition associated with excess accumulation of iron in the subject.

8. The method of claim 1, wherein the iron chelator is administered at the same time as the antisense compound.

9. The method of claim 1, wherein the iron chelator is administered prior to and/or following administration of the antisense compound.

10. The method of claim 7, wherein the disease, disorder, and/or condition is polycythemia.

11. The method of claim 7, wherein the disease, disorder and/or condition is hemochromatosis.

12. The method of claim 7, wherein the disease, disorder and/or condition is anemia.

13. The method of claim 12, wherein the anemia is hereditary anemia, myelodysplastic syndrome or severe chronic hemolysis.

14. The method of claim 13, wherein the hereditary anemia is sickle cell anemia, thalassemia, Fanconi anemia, Diamond Blackfan anemia, Shwachman Diamond syndrome, red cell membrane disorders, glucose-6-phosphate dehydrogenase deficiency, or hereditary hemorrhagic telangiectasia.

15. The method of claim 14, wherein the thalassemia is β-thalassemia.

16. The method of claim 7, wherein the disease, disorder and/or condition is iron overload due to transfusion, excess parenteral iron supplement or dietary iron intake.

17. The method of claim 1, wherein the modified oligonucleotide consists of 12 to 30 linked nucleosides.

18. The method of claim 17, wherein the modified oligonucleotide comprises:
   a gap segment consisting of linked 2'-deoxy nucleosides;
   a 5' wing segment consisting of linked nucleosides;
   a 3' wing segment consisting of linked nucleosides;
   wherein the gap segment is positioned between the 5' wing segment and the 3' wing segment, wherein each nucleoside of each wing segment comprises a modified sugar, and wherein at least one internucleoside linkage of the modified oligonucleotide is a phosphorothioate internucleoside linkage.

19. The method of claim 1, wherein the subject is a human subject.

20. The method of claim 1, wherein accumulation of iron is reduced in the subject following administration of the antisense compound and second agent.

* * * * *